United States Patent
Levine et al.

(10) Patent No.: US 8,920,358 B2
(45) Date of Patent: *Dec. 30, 2014

(54) RESISTIVE ANTI-OBESITY DEVICES

(75) Inventors: Andy H. Levine, Newton, MA (US); Ronald B. Lamport, Pelham, NH (US); David A. Melanson, Hudson, NH (US); Stuart A. Randle, Concord, MA (US)

(73) Assignee: GI Dynamics, Inc., Lexington, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 12/850,185

(22) Filed: Aug. 4, 2010

(65) Prior Publication Data

US 2010/0298632 A1    Nov. 25, 2010

Related U.S. Application Data

(62) Division of application No. 11/330,705, filed on Jan. 11, 2006, now Pat. No. 7,771,382.

(60) Provisional application No. 60/662,570, filed on Mar. 17, 2005, provisional application No. 60/645,296, filed on Jan. 19, 2005.

(51) Int. Cl.
*A61M 5/00* (2006.01)
*A61F 2/04* (2013.01)
*A61F 5/00* (2006.01)

(52) U.S. Cl.
CPC ......... *A61F 5/0079* (2013.01); *A61F 2002/044* (2013.01)
USPC ................. 604/9; 604/8; 606/151; 623/23.64

(58) Field of Classification Search
USPC ............... 606/153, 213, 151, 191; 623/23.64, 623/23.65, 23.68, 23.7, 2.1, 2.11–2.19; 600/32, 37; 128/830, 831, 898; 604/8, 604/9

See application file for complete search history.

(56) References Cited

U.S. PATENT DOCUMENTS

| 4,246,893 A | 1/1981 | Berson |
| 4,265,694 A | 5/1981 | Boretos et al. |

(Continued)

FOREIGN PATENT DOCUMENTS

| EP | 0 506 918 B1 | 1/1996 |
| EP | 0 857 471 A2 | 8/1998 |

(Continued)

OTHER PUBLICATIONS

Rubino, f., et al., "Potential of Surgery for Curing Type 2 Diabetes Mellitus," *Annals of Surgery*, 236(5): 554-559 (2002).

(Continued)

*Primary Examiner* — Dianne Dornbusch
(74) *Attorney, Agent, or Firm* — Hamilton, Brook, Smith & Reynolds, P.C.

(57) ABSTRACT

A patient is provided with an increased sense of satiety by increasing resistance to the outflow of food from the stomach and through the intestines. Stomach emptying may be slowed with devices implantable within the gastrointestinal tract below the stomach. Implants are preferably removable and can include artificial strictures that may be adjustable to vary the rate of stomach emptying. Slowing gastric emptying may induce satiety for a longer period and may therefore reduce food consumption. Many of the embodiments include intestinal liners or sleeves, but they need not. The resistor concept may be applied to a simple anchor and resistor without a long liner.

35 Claims, 18 Drawing Sheets

(56) References Cited

U.S. PATENT DOCUMENTS

| | | | |
|---|---|---|---|
| 4,271,827 A | 6/1981 | Angelchik | |
| 4,315,509 A * | 2/1982 | Smit | 606/108 |
| 4,341,218 A | 7/1982 | Ü | |
| 4,617,932 A | 10/1986 | Kornberg | |
| 4,768,507 A | 9/1988 | Fischell et al. | |
| 4,846,836 A | 7/1989 | Reich | |
| 4,905,693 A | 3/1990 | Ravo | |
| 4,913,141 A | 4/1990 | Hillstead | |
| 5,037,387 A | 8/1991 | Quinn et al. | |
| 5,059,166 A | 10/1991 | Fischell et al. | |
| 5,104,399 A | 4/1992 | Lazarus | |
| 5,123,917 A | 6/1992 | Lee | |
| 5,135,516 A | 8/1992 | Sahatjian et al. | |
| 5,152,782 A | 10/1992 | Kowligi et al. | |
| 5,176,617 A | 1/1993 | Fischell et al. | |
| 5,190,561 A | 3/1993 | Graber | |
| 5,226,429 A | 7/1993 | Kuzmak | |
| 5,254,133 A | 10/1993 | Sied | |
| 5,290,294 A | 3/1994 | Cox et al. | |
| 5,306,300 A * | 4/1994 | Berry | 623/23.64 |
| 5,314,473 A * | 5/1994 | Godin | 623/23.68 |
| 5,322,501 A | 6/1994 | Mahmud-Durrani | |
| 5,330,500 A | 7/1994 | Song | |
| 5,375,612 A * | 12/1994 | Cottenceau et al. | 128/899 |
| 5,389,090 A | 2/1995 | Fischell et al. | |
| 5,405,378 A | 4/1995 | Strecker | |
| 5,417,697 A | 5/1995 | Wilk et al. | |
| 5,423,851 A | 6/1995 | Samuels | |
| 5,480,423 A | 1/1996 | Ravenscroft et al. | |
| 5,492,530 A | 2/1996 | Fischell et al. | |
| 5,605,530 A | 2/1997 | Fischell et al. | |
| 5,607,442 A | 3/1997 | Fischell et al. | |
| 5,634,928 A | 6/1997 | Fischell et al. | |
| 5,639,274 A | 6/1997 | Fischell et al. | |
| 5,643,312 A | 7/1997 | Fischell et al. | |
| 5,669,932 A | 9/1997 | Fischell et al. | |
| 5,695,516 A | 12/1997 | Fischell et al. | |
| 5,697,971 A | 12/1997 | Fischell et al. | |
| 5,720,776 A | 2/1998 | Chuter et al. | |
| 5,722,984 A | 3/1998 | Fischell et al. | |
| 5,730,698 A | 3/1998 | Fischell et al. | |
| 5,733,325 A | 3/1998 | Robinson et al. | |
| 5,735,859 A | 4/1998 | Fischell et al. | |
| 5,735,892 A | 4/1998 | Myers et al. | |
| 5,743,874 A | 4/1998 | Fischell et al. | |
| 5,749,825 A | 5/1998 | Fischell et al. | |
| 5,759,174 A | 6/1998 | Fischell et al. | |
| 5,792,144 A | 8/1998 | Fischell et al. | |
| 5,792,172 A | 8/1998 | Fischell et al. | |
| 5,820,584 A * | 10/1998 | Crabb | 604/500 |
| 5,820,854 A | 10/1998 | Crabb | |
| 5,830,229 A | 11/1998 | Konya et al. | |
| 5,840,009 A | 11/1998 | Fischell et al. | |
| 5,843,164 A | 12/1998 | Frantzen et al. | |
| 5,855,601 A * | 1/1999 | Bessler et al. | 623/2.38 |
| 5,876,445 A | 3/1999 | Andersen et al. | |
| 5,879,282 A | 3/1999 | Fischell et al. | |
| 5,879,370 A | 3/1999 | Fischell et al. | |
| 5,910,145 A | 6/1999 | Fischell et al. | |
| 5,913,895 A | 6/1999 | Burpee et al. | |
| 5,919,233 A | 7/1999 | Knopf et al. | |
| 5,925,063 A | 7/1999 | Khosravi | |
| 5,963,620 A | 10/1999 | Frankel et al. | |
| 5,976,153 A | 11/1999 | Fischell et al. | |
| 6,013,019 A | 1/2000 | Fischell et al. | |
| 6,027,508 A | 2/2000 | Ren et al. | |
| 6,027,526 A | 2/2000 | Limon et al. | |
| 6,086,604 A | 7/2000 | Fischell et al. | |
| 6,102,887 A | 8/2000 | Altman | |
| 6,120,533 A | 9/2000 | Fischell | |
| 6,120,534 A | 9/2000 | Ruiz | |
| 6,146,323 A | 11/2000 | Fischell | |
| 6,152,956 A | 11/2000 | Pierce | |
| 6,179,868 B1 | 1/2001 | Burpee et al. | |
| 6,187,016 B1 | 2/2001 | Hedges et al. | |
| 6,190,403 B1 | 2/2001 | Fischell et al. | |
| 6,221,043 B1 | 4/2001 | Fischell et al. | |
| 6,221,102 B1 | 4/2001 | Baker et al. | |
| 6,241,757 B1 | 6/2001 | An et al. | |
| 6,251,064 B1 | 6/2001 | Silverman et al. | |
| 6,254,642 B1 | 7/2001 | Taylor | |
| 6,270,521 B1 | 8/2001 | Fischell et al. | |
| 6,302,891 B1 | 10/2001 | Nadal | |
| 6,302,917 B1 * | 10/2001 | Dua et al. | 623/23.68 |
| 6,315,708 B1 | 11/2001 | Salmon et al. | |
| 6,355,056 B1 | 3/2002 | Pinheiro | |
| 6,356,782 B1 | 3/2002 | Sirimanne et al. | |
| 6,375,660 B1 | 4/2002 | Fischell et al. | |
| 6,383,214 B1 | 5/2002 | Banas et al. | |
| 6,401,718 B1 | 6/2002 | Johnson et al. | |
| 6,402,779 B1 | 6/2002 | Colone et al. | |
| 6,406,792 B1 | 6/2002 | Briquet et al. | |
| 6,458,074 B1 | 10/2002 | Matsui et al. | |
| 6,485,515 B2 | 11/2002 | Strecker | |
| 6,503,272 B2 * | 1/2003 | Duerig et al. | 623/1.24 |
| 6,520,985 B1 | 2/2003 | Burpee et al. | |
| 6,540,775 B1 | 4/2003 | Fischell et al. | |
| 6,540,789 B1 | 4/2003 | Silverman et al. | |
| 6,544,291 B2 | 4/2003 | Taylor | |
| 6,547,817 B1 | 4/2003 | Fischell et al. | |
| 6,558,429 B2 * | 5/2003 | Taylor | 623/23.68 |
| 6,623,518 B2 | 9/2003 | Thompson et al. | |
| 6,635,069 B1 | 10/2003 | Teoh et al. | |
| 6,635,079 B2 | 10/2003 | Unsworth et al. | |
| 6,645,239 B1 | 11/2003 | Park et al. | |
| 6,652,555 B1 | 11/2003 | VanTassel et al. | |
| 6,669,722 B2 | 12/2003 | Chen et al. | |
| 6,675,809 B2 | 1/2004 | Stack et al. | |
| 6,676,692 B2 | 1/2004 | Rabkin et al. | |
| 6,699,278 B2 | 3/2004 | Fischell et al. | |
| 6,706,061 B1 | 3/2004 | Fischell et al. | |
| 6,716,240 B2 | 4/2004 | Fischell et al. | |
| 6,736,840 B2 | 5/2004 | Fischell et al. | |
| 6,740,121 B2 | 5/2004 | Geitz | |
| 6,764,518 B2 | 7/2004 | Godin | |
| 6,773,440 B2 | 8/2004 | Gannoe et al. | |
| 6,776,791 B1 | 8/2004 | Stallings et al. | |
| 6,802,868 B2 | 10/2004 | Silverman et al. | |
| 6,821,291 B2 | 11/2004 | Bolea et al. | |
| 6,845,776 B2 * | 1/2005 | Stack et al. | 128/898 |
| 6,860,901 B1 | 3/2005 | Baker et al. | |
| 6,936,065 B2 | 8/2005 | Khan et al. | |
| 6,960,233 B1 | 11/2005 | Berg et al. | |
| 7,011,673 B2 | 3/2006 | Fischell et al. | |
| 7,025,791 B2 | 4/2006 | Levine et al. | |
| 7,037,327 B2 | 5/2006 | Salmon et al. | |
| 7,037,344 B2 | 5/2006 | Kagan et al. | |
| 7,081,132 B2 | 7/2006 | Cook et al. | |
| 7,087,088 B2 | 8/2006 | Berg et al. | |
| 7,118,600 B2 * | 10/2006 | Dua et al. | 623/23.68 |
| 7,121,283 B2 | 10/2006 | Stack et al. | |
| 7,122,058 B2 * | 10/2006 | Levine et al. | 623/23.65 |
| 7,146,984 B2 | 12/2006 | Stack et al. | |
| 7,152,607 B2 * | 12/2006 | Stack et al. | 128/898 |
| 7,160,312 B2 | 1/2007 | Saadat | |
| 7,175,660 B2 | 2/2007 | Cartledge et al. | |
| 7,211,114 B2 | 5/2007 | Bessler et al. | |
| 7,220,237 B2 | 5/2007 | Gannoe et al. | |
| 7,220,284 B2 | 5/2007 | Kagan et al. | |
| 7,267,694 B2 | 9/2007 | Levine et al. | |
| 7,314,489 B2 * | 1/2008 | McKenna et al. | 623/23.65 |
| 7,316,663 B2 * | 1/2008 | Whitmore, III | 604/8 |
| 7,316,716 B2 * | 1/2008 | Egan | 623/23.65 |
| 7,329,285 B2 | 2/2008 | Levine et al. | |
| 7,335,210 B2 * | 2/2008 | Smit | 606/108 |
| 7,338,520 B2 | 3/2008 | Bailey et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 7,666,180 B2 * | 2/2010 | Holsten et al. | 606/1 |
| 8,038,720 B2 | 10/2011 | Wallace et al. | |
| 2001/0020190 A1 | 9/2001 | Taylor | |
| 2002/0022853 A1 | 2/2002 | Swanson et al. | |
| 2002/0032487 A1 | 3/2002 | Dua et al. | |

(56) References Cited

U.S. PATENT DOCUMENTS

| | | | |
|---|---|---|---|
| 2002/0049468 A1* | 4/2002 | Streeter et al. | 606/200 |
| 2002/0065545 A1 | 5/2002 | Leonhardt et al. | |
| 2002/0091439 A1 | 7/2002 | Baker et al. | |
| 2002/0147489 A1 | 10/2002 | Hong et al. | |
| 2002/0183786 A1 | 12/2002 | Girton | |
| 2002/0188344 A1 | 12/2002 | Bolea et al. | |
| 2002/0188354 A1 | 12/2002 | Peghini | |
| 2003/0040804 A1* | 2/2003 | Stack et al. | 623/23.7 |
| 2003/0040808 A1 | 2/2003 | Stack et al. | |
| 2003/0060894 A1* | 3/2003 | Dua et al. | 623/23.68 |
| 2003/0109931 A1 | 6/2003 | Geitz | |
| 2003/0153927 A1 | 8/2003 | DiPoto et al. | |
| 2003/0191476 A1 | 10/2003 | Smit | |
| 2003/0199991 A1 | 10/2003 | Stack et al. | |
| 2003/0216749 A1 | 11/2003 | Ishikawa et al. | |
| 2004/0019388 A1 | 1/2004 | StarkEbaum | |
| 2004/0037865 A1 | 2/2004 | Miller | |
| 2004/0039452 A1 | 2/2004 | Bessler | |
| 2004/0082963 A1 | 4/2004 | Gannoe et al. | |
| 2004/0092892 A1 | 5/2004 | Kagan et al. | |
| 2004/0092974 A1 | 5/2004 | Gannoe et al. | |
| 2004/0093065 A1 | 5/2004 | Yachia et al. | |
| 2004/0102855 A1* | 5/2004 | Shank | 623/23.68 |
| 2004/0107004 A1 | 6/2004 | Levine et al. | |
| 2004/0117004 A1 | 6/2004 | Osborne et al. | |
| 2004/0117031 A1 | 6/2004 | Stack et al. | |
| 2004/0122470 A1 | 6/2004 | Deem et al. | |
| 2004/0122526 A1 | 6/2004 | Imran | |
| 2004/0138761 A1 | 7/2004 | Stack et al. | |
| 2004/0151740 A1 | 8/2004 | Aoki et al. | |
| 2004/0158229 A1 | 8/2004 | Quinn | |
| 2004/0172142 A1 | 9/2004 | Stack et al. | |
| 2004/0181242 A1 | 9/2004 | Stack et al. | |
| 2004/0193093 A1 | 9/2004 | Desmond, III | |
| 2004/0193261 A1 | 9/2004 | Berreklouw | |
| 2004/0210243 A1 | 10/2004 | Gannoe et al. | |
| 2004/0220682 A1* | 11/2004 | Levine et al. | 623/23.65 |
| 2004/0236401 A1 | 11/2004 | Shin et al. | |
| 2004/0249362 A1 | 12/2004 | Levine et al. | |
| 2005/0004681 A1 | 1/2005 | Stack et al. | |
| 2005/0010246 A1* | 1/2005 | Streeter et al. | 606/200 |
| 2005/0033331 A1 | 2/2005 | Burness et al. | |
| 2005/0043601 A1 | 2/2005 | Kilcoyne et al. | |
| 2005/0043817 A1 | 2/2005 | McKenna et al. | |
| 2005/0049718 A1 | 3/2005 | Dann et al. | |
| 2005/0055039 A1 | 3/2005 | Burnett et al. | |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085787 A1 | 4/2005 | Laufer | |
| 2005/0085923 A1* | 4/2005 | Levine et al. | 623/23.65 |
| 2005/0090873 A1 | 4/2005 | Imran | |
| 2005/0096750 A1 | 5/2005 | Kagan et al. | |
| 2005/0111072 A1 | 5/2005 | Miyagaki et al. | |
| 2005/0125020 A1* | 6/2005 | Meade et al. | 606/191 |
| 2005/0125075 A1* | 6/2005 | Meade et al. | 623/23.64 |
| 2005/0149114 A1 | 7/2005 | Cartledge et al. | |
| 2005/0171556 A1 | 8/2005 | Murphy | |
| 2005/0192614 A1 | 9/2005 | Binmoeller | |
| 2005/0216040 A1 | 9/2005 | Gertner et al. | |
| 2005/0216042 A1 | 9/2005 | Gertner | |
| 2005/0228415 A1 | 10/2005 | Gertner | |
| 2005/0228504 A1 | 10/2005 | Demarais | |
| 2005/0240279 A1 | 10/2005 | Kagan et al. | |
| 2005/0256587 A1* | 11/2005 | Egan | 623/23.65 |
| 2005/0267405 A1 | 12/2005 | Shah | |
| 2005/0267499 A1 | 12/2005 | Stack et al. | |
| 2005/0267533 A1 | 12/2005 | Gertner | |
| 2006/0009858 A1 | 1/2006 | Levine et al. | |
| 2006/0064120 A1 | 3/2006 | Levine et al. | |
| 2006/0106332 A1 | 5/2006 | Knudson et al. | |
| 2006/0155312 A1 | 7/2006 | Levine et al. | |
| 2006/0161172 A1 | 7/2006 | Levine et al. | |
| 2006/0161187 A1 | 7/2006 | Levine et al. | |
| 2006/0161265 A1 | 7/2006 | Levine et al. | |
| 2006/0212042 A1 | 9/2006 | Lamport et al. | |
| 2006/0265082 A1 | 11/2006 | Meade et al. | |
| 2006/0271175 A1 | 11/2006 | Woolfson et al. | |
| 2006/0287734 A1 | 12/2006 | Stack et al. | |
| 2007/0005147 A1 | 1/2007 | Levine et al. | |
| 2007/0010864 A1 | 1/2007 | Dann et al. | |
| 2007/0027548 A1 | 2/2007 | Levine et al. | |
| 2007/0032879 A1 | 2/2007 | Levine et al. | |
| 2007/0049801 A1 | 3/2007 | Lamport et al. | |
| 2007/0083271 A1 | 4/2007 | Levine et al. | |
| 2007/0282453 A1 | 12/2007 | Weitzner et al. | |
| 2007/0293885 A1 | 12/2007 | Binmoeller | |
| 2008/0071383 A1 | 3/2008 | Levine et al. | |
| 2008/0097466 A1 | 4/2008 | Levine et al. | |
| 2008/0103604 A1 | 5/2008 | Levine et al. | |
| 2008/0208239 A1 | 8/2008 | Annunziata | |
| 2008/0208357 A1 | 8/2008 | Melanson et al. | |
| 2008/0223476 A1 | 9/2008 | Stinson | |
| 2008/0234834 A1 | 9/2008 | Meade et al. | |
| 2009/0177215 A1 | 7/2009 | Stack et al. | |
| 2013/0253410 A1 | 9/2013 | Levine et al. | |

FOREIGN PATENT DOCUMENTS

| | | |
|---|---|---|
| EP | 0935977 A2 | 8/1999 |
| EP | 0935977 A3 | 8/1999 |
| EP | 1481649 A1 | 12/2004 |
| EP | 1 504 778 A2 | 2/2005 |
| EP | 1 504 778 A3 | 3/2005 |
| WO | WO 92/06734 A1 | 4/1992 |
| WO | WO 95/05132 | 2/1995 |
| WO | WO 97/03624 A1 | 2/1997 |
| WO | WO 98/22045 | 5/1998 |
| WO | WO 99/23953 | 5/1999 |
| WO | WO 99/44536 | 9/1999 |
| WO | WO 00/32137 | 6/2000 |
| WO | WO 00/42945 | 7/2000 |
| WO | WO 01/12256 A1 | 2/2001 |
| WO | WO 01/35861 A1 | 5/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064682 A1 | 8/2004 |
| WO | WO 2004/069332 A1 | 8/2004 |
| WO | WO 2004/073782 A1 | 9/2004 |
| WO | WO 2004/080336 A | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/009288 A2 | 2/2005 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 | 12/2005 |
| WO | WO 2005/118049 | 12/2005 |
| WO | WO 2005/120363 | 12/2005 |
| WO | WO 2006/016894 A1 | 2/2006 |
| WO | WO 2006/034062 A1 | 3/2006 |
| WO | WO 2006/078781 | 7/2006 |
| WO | WO 2006/078927 | 7/2006 |

(56) References Cited

FOREIGN PATENT DOCUMENTS

| WO | WO 2006/088578 A1 | 8/2006 |
|---|---|---|
| WO | WO 2006/102012 A1 | 9/2006 |
| WO | WO 2006/133311 A2 | 12/2006 |

OTHER PUBLICATIONS

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11, Jan. 2004.

Choostent™, Covered Esophageal Stent, Instructions, Retrieved from the Internet (http://mitech.co.kr/uploads/images/282/use guide esophachoo_english.pdf) on Jul. 26, 2005.

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul.-Aug. 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stents[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

U.S. Office Action dated Jan. 15, 2010 for U.S. Appl. No. 11/827,674.

International Search Report in International Application No. PCT/US2006/001842, "Resistive Anti-Obesity Devices," mailed on Jun. 13, 2006.

International Preliminary Report on Patentability in International Application No. PCT/US2006/001842, "Resistive Anti-Obesity Devices," mailed on Jul. 24, 2007.

U.S. Appl. No. 13/896,956, "Resistive Anti-Obesity Devices," filed May 17, 2013.

\* cited by examiner

*FIGURE 4A*
*FIGURE 4B*
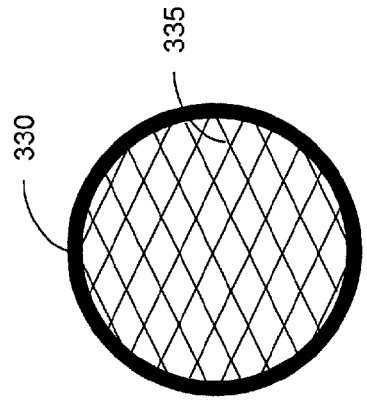
*FIGURE 4D*
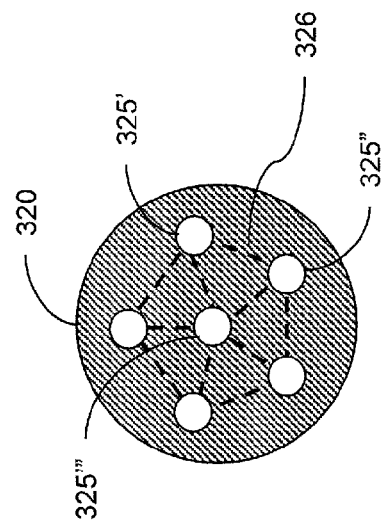
*FIGURE 4C*

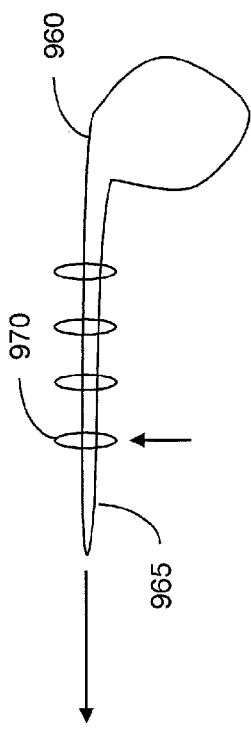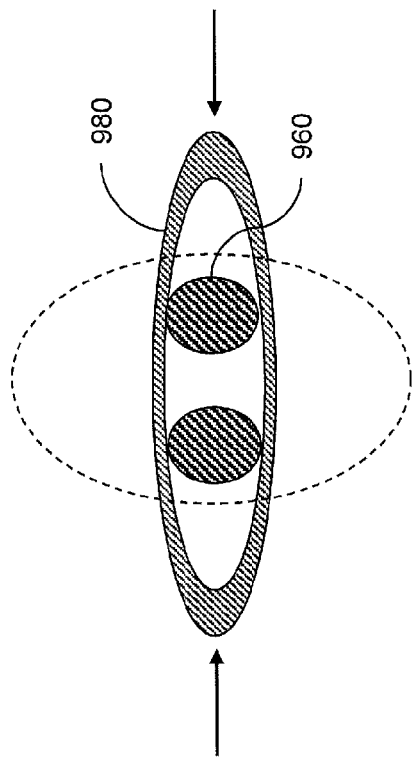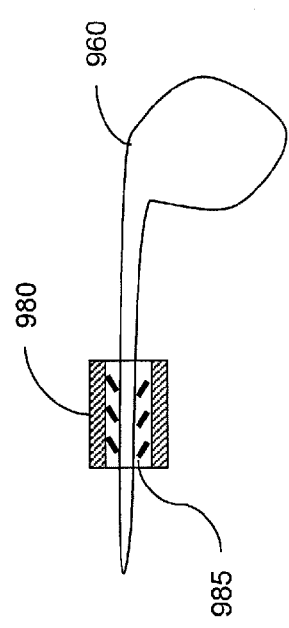
FIGURE 10C
FIGURE 10D
FIGURE 10E

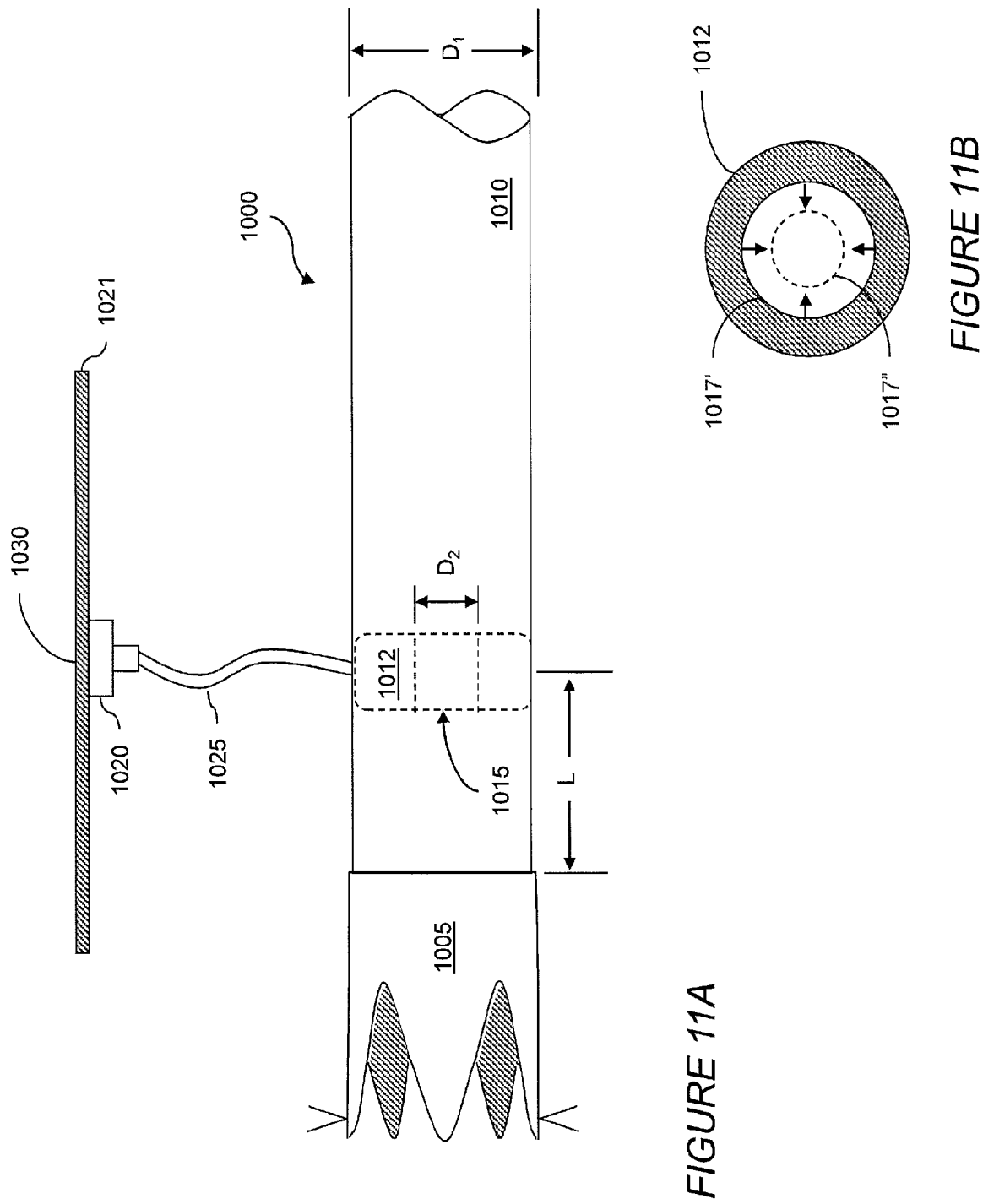

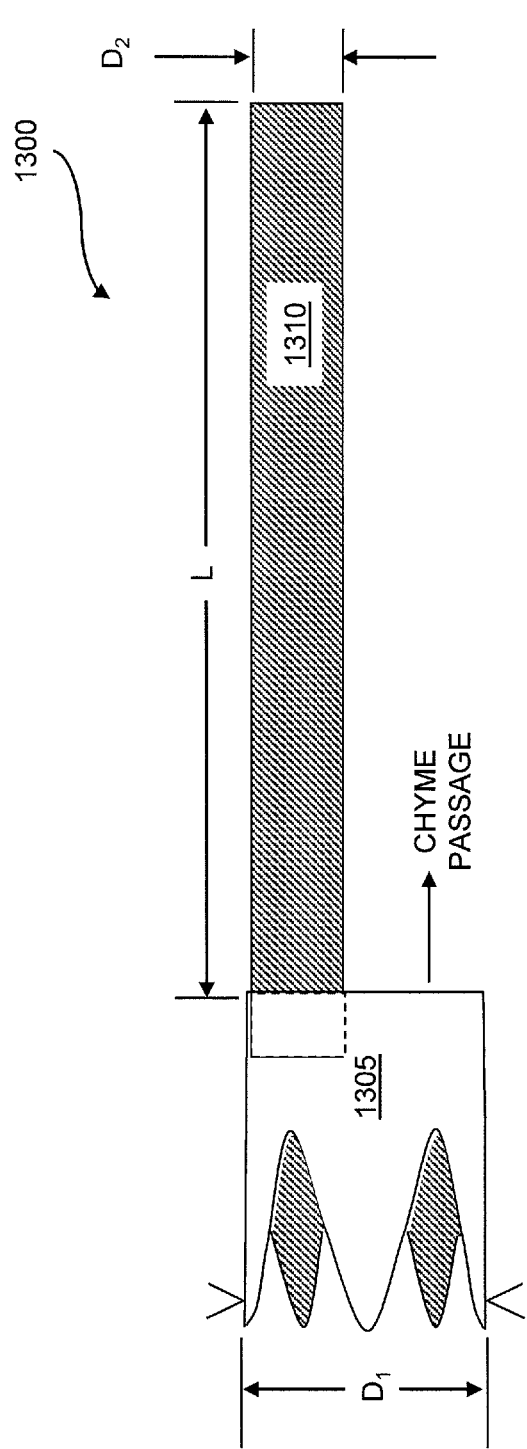
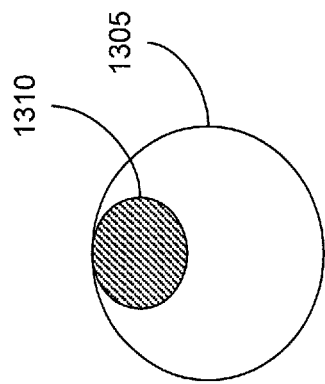
*FIGURE 14A*
*FIGURE 14B*

RESISTIVE ANTI-OBESITY DEVICES

RELATED APPLICATIONS

This application is a divisional of U.S. application Ser. No. 11/330,705, filed Jan. 11, 2006, now U.S. Pat. No. 7,771,382, which claims the benefit of U.S. Provisional Application No. 60/662,570, filed on Mar. 17, 2005 and U.S. Provisional Application No. 60/645,296, filed on Jan. 19, 2005.

The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the United States with a Body Mass Index (BMI) of 30 or above. The BMI is defined as a person's weight (in kilograms) divided by height (in meters), squared. To be considered clinically, morbidly obese, one must meet one of three criteria: BMI over 35, 100 pounds overweight, or 100% above ideal body weight. There is also a category for the super-obese for those weighing over 350 pounds.

Obesity is an overwhelming health problem. Because of the enormous strain associated with carrying this excess weight, organs are affected, as are the nervous and circulatory systems. In 2000, the National Institute of Diabetes, Digestive, and Kidney Diseases (NIDDK) estimated that there were 280,000 deaths directly related to obesity. The NIDDK further estimated that the direct cost of healthcare in the U.S. associated with obesity is $51 billion. In addition, Americans spend $33 billion per year on weight loss products. In spite of this economic cost and consumer commitment, the prevalence of obesity continues to rise at alarming rates. From 1991 to 2000, obesity in the U.S. grew by 61%. Not exclusively a U.S. problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach staplings, or gastroplasties, to reduce the volumetric size of the stomach, thereby achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

Surgeries can generally be separated into restrictive procedures, malabsorptive procedures and combinations thereof. At least two surgical procedures that successfully produce long-term weight loss are the Roux-en-Y gastric bypass, and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods.

The Laparoscopic Adjustable Gastric Band is a device that is placed around the top of the stomach to create a restriction. This forces the patient to eat smaller meals as the food must pass from the small pouch into the rest of the stomach before he/she can eat again. This device however does require surgery for its placement and is difficult to remove.

These procedures carry a heavy toll. The morbidity rate for bariatric surgical procedures is alarmingly high with 11% requiring surgical intervention for correction. Early small bowel obstruction occurs at a rate of between 2-6% in these surgeries and mortality rates are reported to be approximately 0.5-1.5%. While surgery is effective, the current invasive procedures are not acceptable with these complication rates. Laparoscopic techniques applied to these surgeries result in fewer surgical complications but continue to expose these very ill patients to high operative risk in addition to requiring an enormous level of skill by the surgeon. Devices to reduce absorption in the small intestines have been proposed (see U.S. Pat. No. 5,820,584 (Crabb), U.S. Pat. No. 5,306,300 (Berry) and U.S. Pat. No. 4,315,509 (Smit)). However, these devices have not been successfully implemented. Restrictive devices include Laparoscopic Adjustable Gastric Banding (LABG) (see for example U.S. Pat. No. 5,226,429 (Kuzmak)) and gastric balloons (see for example U.S. Pat. No. 4,823,808 (Clegg et al.) and U.S. Pat. No. 6,755,869 (Geitz)).

SUMMARY OF THE INVENTION

The present invention relates to methods, devices and systems that provide an increased sense of satiety to a person by increasing the resistance to the outflow of food from the stomach. Gastric emptying can be slowed using devices that slow the passage of chyme through the intestines. Slowing gastric emptying may induce satiety for a longer period and may therefore reduce food consumption. Although many of these concepts include intestinal liners, they need not. The resistor concept may be applied to a simple anchor and resistor without a long liner.

Restrictive devices have been previously described but most commonly are described to reside within the stomach. Anchoring devices in the stomach is difficult as the stomach is a particularly active region of the anatomy tending to tear out devices implanted therein. The devices described herein are more typically anchored in the intestines.

Devices which include liners can be implanted within the intestine to prevent the contact of partially-digested food (i.e., chyme) with the intestine thereby reducing one or more of hormone triggers, digestion and absorption of nutrients. By adding a resistive feature to these devices passage of chyme through the device can be slowed. By reducing the flow below a rate at which chyme flows in an unrestricted intestine, the chyme can build up along a proximal end of the device. The chyme build-up slows the gastric emptying process, as there will be less volume available within the intestine to accommodate additional chyme from the stomach, or the pressure required to pass the chyme from the stomach to the intestine is higher than normal.

It is believed that slowing emptying of the stomach may ultimately reduce the amount of food a patient consumes. Alternatively or in addition, an intestinal implant device creating a resistance within the intestine requires the bowel to exert more energy to propel the chyme than would otherwise be necessary without the resistance. Such a restriction can slow gastric emptying, cause higher energy expenditure, and lead to weight loss.

Methods are provided for inducing weight loss within a patient by treating a region of the intestine below the pyloric sphincter and slowing gastric emptying responsive to the treated region, resulting in a prolonged feeling of satiety by the patient. The treatment can include implanting at least a portion of a device below the pyloric sphincter. Preferably, the implanted device reduces the flow of chyme into the proximal intestine. For example, the device provides an artificial stricture through which the chyme passes. The artificial stricture can include a diaphragm narrowing the intestinal lumen. The diaphragm can include a membrane defining a reduced aperture. Alternatively or in addition, the artificial stricture can include a liner defining a central lumen through which chyme passes, the artificial stricture being coupled to the liner.

In some embodiments, the artificial stricture is adjustable. For example, the stricture can be formed using an adjustable member coupled to adjust the diameter of the interior lumen of a liner. The adjustable member can be combined with a securing feature adapted for adjustably securing the adjustable member in place once a desired restriction is achieved. In other embodiments, the adjustable member includes a balloon that can be adjusted by inflation and deflation.

In other embodiments, the restrictive element is elastomeric and passively controls the outlet pressure of the stomach by varying in diameter depending on the inlet pressure.

In other embodiments, the implanted device includes a dampening liner adapted to reduce peristaltic efficiency. The dampening liner can be a semi-rigid liner. In yet another embodiment, the implanted device occupies a non-negligible volume within the intestine, thereby reducing the available intestinal volume and limiting the amount of chyme that can be accommodated.

Alternatively or in addition, the present invention relates to a gastrointestinal implant including a resistive feature adapted to be secured within the intestine and distal to the pyloric sphincter. When implanted, the resistive feature impedes gastric emptying. An anchor can be coupled to the resistive feature for attaching the resistive feature to the gastrointestinal tract. In some embodiments, the resistive feature includes a sleeve or liner defining a central lumen through which chyme can pass. The liner itself can define a central lumen having a constricted region of a reduced diameter.

In another embodiment the gastrointestinal implant includes a resistive coating provided on an interior surface of the liner. For example, the resistive coating can include artificial cilia aligned to impede the passage of chyme. In yet other embodiments, the resistive feature includes a bent wire, such as a contorted wire formed from a resilient wire, such as Nitinol wire.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4D are end views showing alternative types of restrictive members used in the embodiment of the invention shown in FIG. 3;

FIG. 10C is a schematic diagram illustrating a side view of an embodiment of a crimp-type locking mechanism for locking the drawstring of FIGS. 9A-9D;

FIG. 10D is a schematic diagram illustrating a cross-sectional side view of an embodiment of a friction locking mechanism for locking the drawstring of FIGS. 9A-9D;

FIG. 10E is a schematic diagram illustrating an axial cross section of the embodiment shown in FIG. 10D;

FIG. 11A is a schematic diagram illustrating a side view of an embodiment of the invention including an inflatable restrictive member;

FIG. 11B is a schematic diagram illustrating an end view of the inflatable restrictive member shown in FIG. 11A;

FIG. 14A is a schematic diagram illustrating a side view of an embodiment of the invention including a solid mass within the intestine;

FIG. 14B is a schematic diagram illustrating an end view of the embodiment including a solid-mass shown in FIG. 14A;

DETAILED DESCRIPTION OF THE INVENTION

A description of preferred embodiments of the invention follows.

This general concept relates to providing an increased sense of satiety by slowing gastric emptying by providing resistance to the outflow of food from the stomach and through the intestines. An increased sense of satiety is obtained by slowing emptying of an animal's stomach. Gastric emptying can be slowed by providing resistance to the outflow of food, or chyme, from the stomach. In general, an animal perceives a sensation of satiety when the stomach fills. It is believed that by slowing gastric emptying into the duodenum, an animal can maintain a feeling of satiety for a longer period of time. Consequently, an animal no longer feeling hungry will tend to eat less.

There are several approaches that can be used to increase resistance to flow of the chyme. For example, a device having features adapted to resist the flow of chyme can be implanted within the gastrointestinal tract distal to the stomach. At least one approach is simply placing a sleeve or liner within the intestine. The mere presence of the liner can add some resistance to the flow of chyme therethrough.

Alternatively or in addition, an implant can include at least one resistive feature, such as a reduced-diameter aperture, or stricture, that artificially narrows a region of the gastrointestinal tract. A resistive implant is preferably placed at a predetermined location within the body and adapted to remain there throughout a course of treatment. To maintain the implant in place, at least a portion of the device is secured to the surrounding anatomy. Securing of an implant can be accomplished using an anchor coupled to the device. Anchoring within the gastrointestinal tract, however, poses numerous challenges due at least in part to the physiology of the anatomical region, its high degree of motility, and pressures resulting from digestive forces.

One region of the gastrointestinal tract that is particularly well suited for anchoring the resistive implant is the proximal duodenum. Compared to the stomach, the pylorus, and even distal regions of the small intestine, the proximal duodenum is relatively immotile. Additionally, the proximal duodenum defines a slightly enlarged cavity just distal to the pyloric sphincter referred to as the duodenal bulb. An anchor of the type shown in FIG. 1A that expands to conform to the lumen is particularly well suited for positioning within the bulbous duodenum. The shape of the cavity and its relatively low motility will enhance performance of the anchoring device.

Figure 1B:
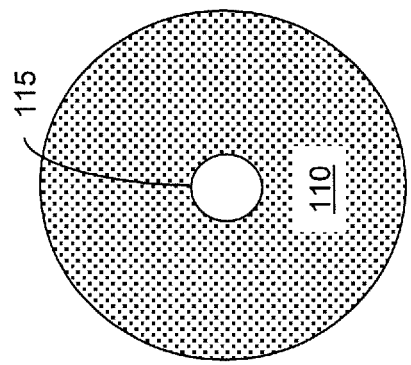
FIG. 1B is a schematic diagram of an end view of the embodiment of FIG. 1A.
Figure 1A:
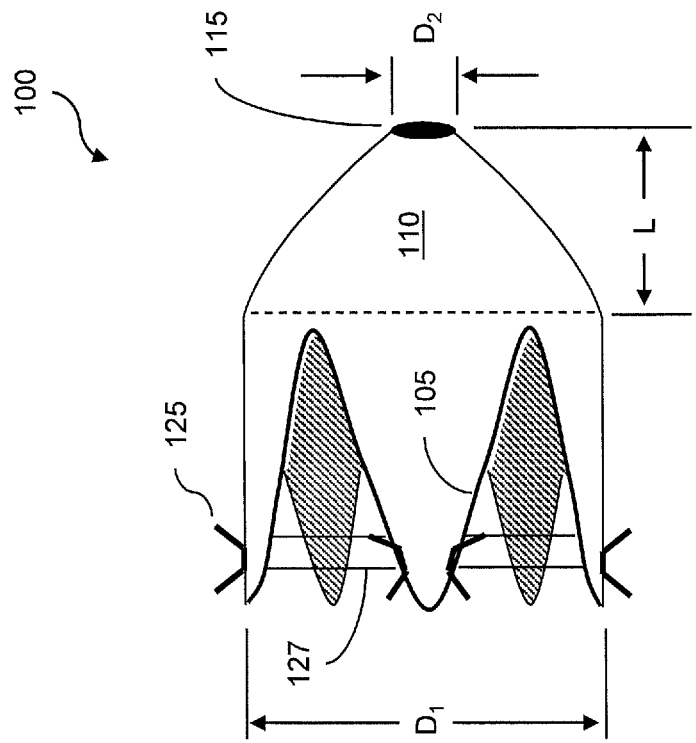
FIG. 1A is a schematic diagram illustrating a side view of the embodiment of the invention including an artificial stricture.

An exemplary artificial stricture 100 adapted for gastrointestinal applications is illustrated in FIG. 1. The device 100 includes an anchoring element 105 coupled to an artificial stricture. The artificial stricture retards the flow of chyme therethrough. The anchor 105 is adapted to anchor the device 100 within the gastrointestinal tract. When placed at or below the pylorus, the stricture operates to slow gastric emptying. The anchor is adapted to hold the device securely in place under gastrointestinal forces and pressures.

The anchor can be a radial spring defining an opening therethrough for the passage of chyme and adapted to engage the surrounding tissue of the hollow organ within which it is implanted. Thus, the anchor 105 can provide an interference fit to the surrounding tissue. In some embodiments, the perimeter of the anchor is in sealable communication with the surrounding tissue of the lumen to prevent leakage of chyme and fluids beyond the artificial stricture.

The artificial stricture can be formed from a blocking material 110 coupled to the anchor 105, the blocking material defining an aperture 115 therein. For example, the blocking material can include the same materials described in more detail below in reference to intestinal liners. The blocking material is dimensioned to at least cover the cross-sectional area of the lumen within which it is implanted. For an implant adapted for use in the proximal duodenum of an adult male, the diameter of the impermeable material would be at least about 25 millimeters.

The stricture is created by forming an aperture 115 having a reduced cross-sectional area, or diameter within the blocking material 110. The aperture can be formed, for example, by simply cutting or punching a hole of the appropriate dimensions into the blocking material 110. For example, the hole can be less than about 10 millimeters in diameter for the exemplary 25 millimeter implant. In some embodiments, the aperture is about 5 millimeters in diameter or less. It is unlikely, however, that an orifice of less than about 2 millimeters would be used in a human application as food particle passing through the pylorus are typically about 1-2 millimeters or less in size.

Figure 2:
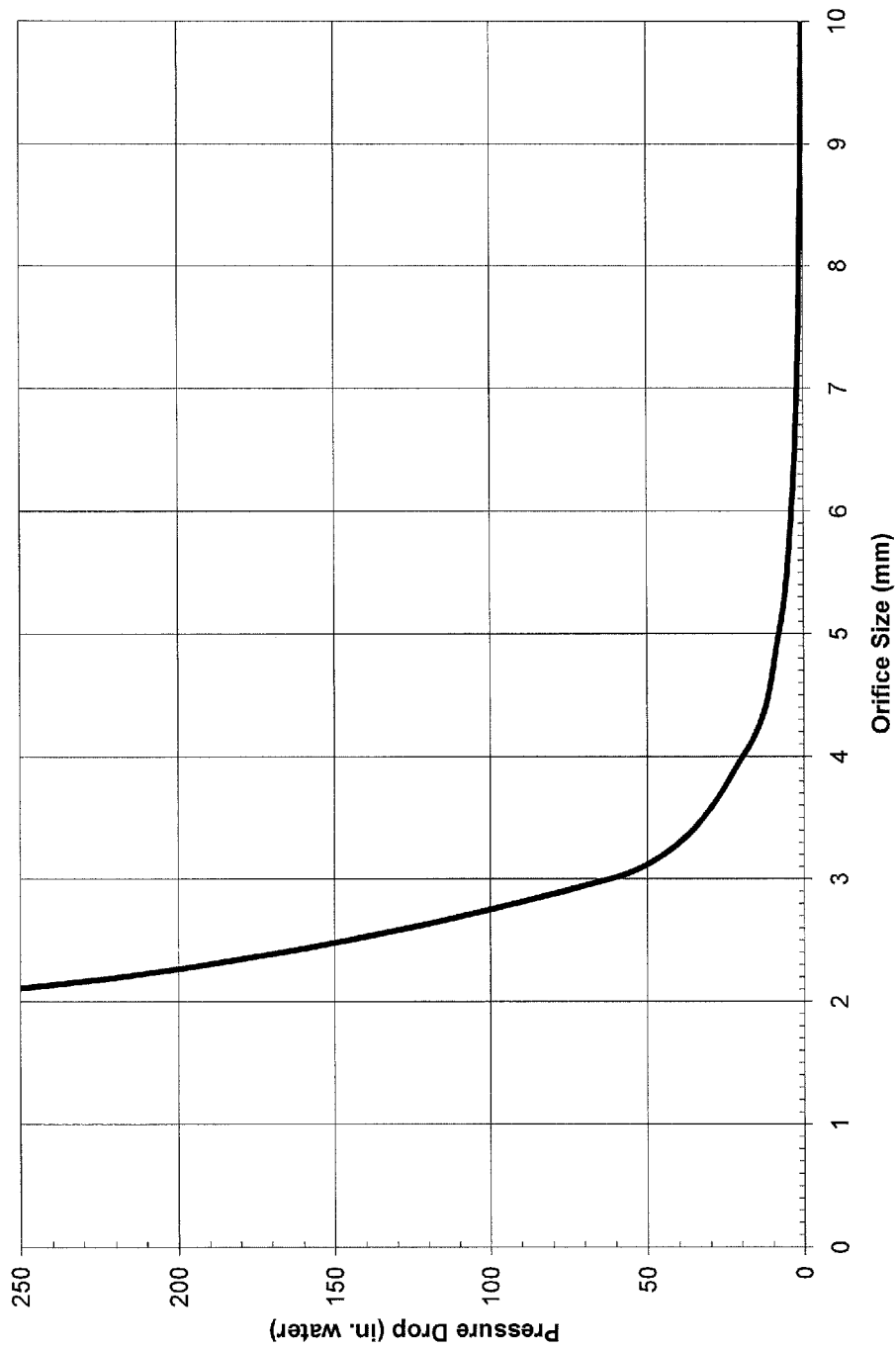
FIG. 2 is a graph illustrating the pressure drop of an exemplary fluid through an orifice of varying size.

Fluid mechanics can be used to determine the size orifice needed to provide a restriction within the duodenum. For example, the Bernoulli equation can be applied to the flow of a Newtonian fluid through an orifice as provided in equation 1. In this equation, ΔP represents the pressure drop across the orifice, ρ corresponds to the fluid density, Q corresponds to the volume flow (determined as the product of the fluid velocity and the flow area), D is the diameter of the unobstructed opening (e.g., about 25 mm in the example of FIG. 2), and d is the diameter of the orifice in millimeters. In the example of FIG. 2, the diameter of the orifice is varied between about 2 and 10 mm.

$$\Delta P = (8\rho Q^2)/(\pi^2 D^4) * [(D/d)^4 - 1] \qquad (1)$$

An exemplary graph of the pressure drop through an orifice of varying size is provided in FIG. 2. The graph was determined by applying equation 1 using an assumed velocity of about 2 cm/sec, which corresponds to the mean flow rate of chyme through the intestines. Considering peristaltic pressures on the order of 20-40 inches of water (an exemplary range of pressures corresponding to an adult human) the orifice size should be less than about 5 mm in diameter to provide flow resistance. More preferably, the orifice size is less than 5 mm. For example, an orifice of about 3 mm provides increased flow resistance under nominal anticipated peristaltic pressures.

In some embodiments, the aperture is adjustable. For example, an aperture can be increased by stretching it until the blocking material defining the aperture plastically deforms to a new, larger diameter. Stretching can be accomplished using a balloon inserted into the aperture, the balloon being inflated after insertion. The pressure of the inflated balloon will stretch a suitable blocking material to a larger size. When the balloon is removed, the material will retain the enlarged aperture. In other embodiments, the blocking material is elastomeric such that the aperture is permitted to temporarily expand above certain pressures to prevent blockage of the aperture for food particles larger than the minimum dimension the aperture returning to its reduced diameter thereafter.

Referring again to FIG. 1, the anchor 105 generally defines a central lumen through which chyme flows. The anchor, which can be at or distal to the pylorus, can include a stent, such as the stents described in U.S. patent application Ser. No. 10/339,786 filed on Jan. 9, 2003 (now U.S. Pat. No. 7,025,791), incorporated herein by reference in its entirety. Alternatively or in addition, the anchor can include a radial spring, such as the wave anchor illustrated and described in more detail in U.S. patent application Ser. No. 10/858,851 filed on Jun. 1, 2004 (now U.S. Pat. No. 7,476,256) and incorporated herein by reference in its entirety. The anchor can be self-expanding and can have a relaxed diameter of at least 40 mm or of at least 45 mm.

The anchor 105 can attach to the intestine using a frictional or interference fit. Thus, the anchor can have a relaxed diameter that is greater than the maximum anticipated diameter of the intestine, such that the anchor will provide an outward force against the adjacent anatomy acting to keep the anchor in place. Alternatively or in addition, the anchor 105 can include one or more external barbs 125 further securing the implant device in the presence of peristalsis. Preferably, the barbs 125 are sized and positioned to engage muscular tissue. Exemplary barbs are described in more detail in U.S. patent application Ser. No. 10/339,786 filed on Jan. 9, 2003 (now U.S. Pat. No. 7,025,791), and U.S. patent application Ser. No. 10/858,852 filed on Jun. 1, 2004 (now U.S. Pat. No. 7,815,589), incorporated herein by reference in its entirety.

The anchor 100 can also include one or more repositioning features. As shown the device includes a drawstring 127 at its proximal end. The drawstring 127 is threaded through the open end of the anchor 100 such that it can be grasped and used to facilitate repositioning of the anchor 100 within the body or removal of the anchor 100 from the body. Removal methods and devices using a drawstring are described in U.S. application Ser. No. 11/318,083, entitled "Removal and Repositioning Device" filed on Dec. 22, 2005 and incorporated herein by reference in its entirety.

In some embodiments, an anchor is attached to a material similar to the blocking material. For example, the anchor can be encapsulated between overlapping layers of a tubular segment of blocking material. The blocking material 110 defining the aperture 115 can then be formed in the same blocking material that is attached to the anchor 105. Alternatively, a different blocking material can be used.

The blocking material 110 can first be formed into a suitable pattern, such as the circle shown and then attached to the anchor and/or to material covering the anchor 105. When the anchor 105 is also attached to the blocking material, the different segments of blocking material can be sealably attached together using any suitable means. For example, the blocking material 110 can be attached to the anchor covering by suturing. Alternatively or in addition, the blocking material 110 can be attached to the anchor covering by a chemical fastener, such as an adhesive, and/or by thermal bonding. Formed in this manner, the attached blocking material 110 may extend for some distance L from the distal end of the anchor 105 when in the presence of a proximal pressure (e.g., the material bulges out in an elongated or domed fashion). In some embodiments, the blocking material 110 is attached in a relatively taught manner, similar to the skin of a drum to limit any axial extent L of the blocking material 110 beyond the distal end of the anchor 105.

Figure 3:
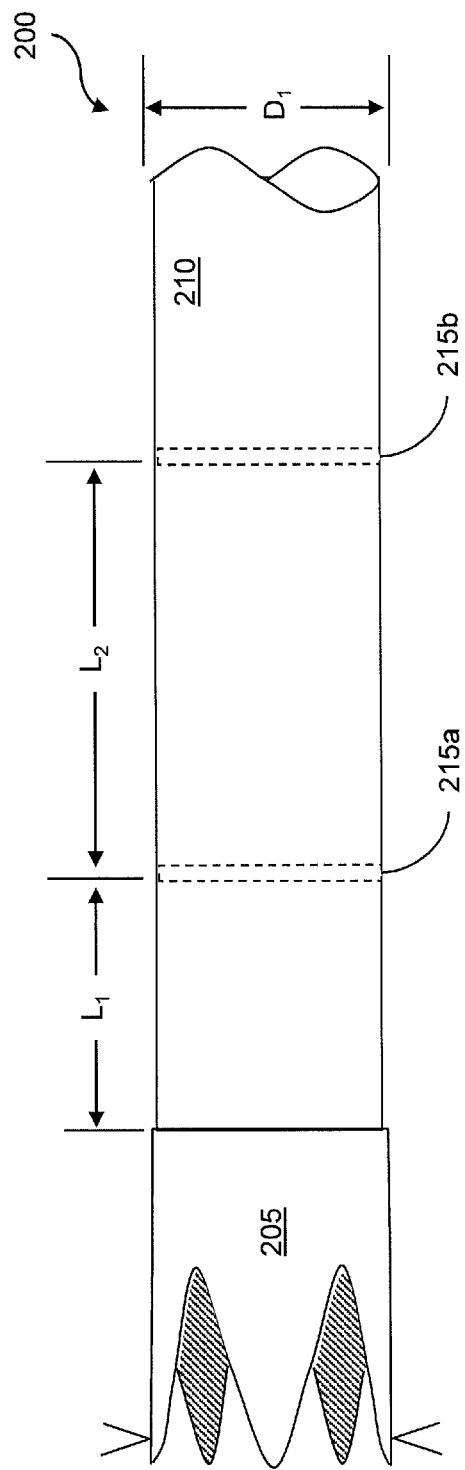
FIG. 3 is a side view of an embodiment of the invention including a liner having one or more restrictive members.

In some embodiments, the resistive implant includes a liner. As shown in FIG. 3, an implant device 200 includes an elongated liner 210 adapted for placement within a hollow organ, such as the intestine. In some embodiments, the implant 200 includes an anchor 205 coupled to the liner 210, with the anchor 205 adapted to secure at least a portion of the liner 210 within the lumen of the intestine. For example, a hollow anchor similar to those anchors described above can be attached to the proximal end of the liner 210 to secure the proximal end of the liner 210 to the surrounding tissue of the intestine. Once implanted, the liner 210 is extended distally from the anchor along the intestine.

Preferably, any of the implantable devices described herein can be configured to be removable. Thus, any permanence of a resistive device only applies during the period in which the device is implanted within the patient. Thus, a resistive device can be removed should the need arise. Alternatively or in addition, a different or even the same resistive device can be re-implanted within the same patient.

The liner 210 can be formed from a thin yet durable biocompatible material and is generally unsupported and tending to collapse upon itself when empty. For example, the liner 210 can be formed from a fluoropolymer, such as expanded polytetrafluoroethylene (ePTFE). In some embodiments, the liner material is formed using a combination of different materials, such as ePTFE with a different fluoropolymer such as fluorinated ethylene propylene (FEP). The combination of ePTFE and FEP provides a low coefficient of friction, while also being substantially non-permeable. Alternatively or in addition, the liner is formed using polyolefin (e.g., LPDE, HPDE, polypropylene) films. Gastrointestinal liners are described in more detail in U.S. patent application Ser. No. 10/339,786 filed on Jan. 9, 2003 (now U.S. Pat. No. 7,025,791), incorporated herein by reference in its entirety.

The liner 210 can have a diameter corresponding to the nominal expanded diameter of the lumen within which it is implanted. Current liners being used in porcine testing include diameters of about 25 millimeters, believed to be close to the diameter of the bowel. A liner having a similar diameter is also believed to be suitable for use within the proximal portion of the small intestine of an adult human. The length of the liner can vary from centimeters to a meter or more depending upon the particular application.

The liner 210 provides the added feature of preventing contact between the intestinal walls and any chyme contained therein. The liner can also delay the mixing of chyme with digestive enzymes secreted within the intestine.

In some embodiments, the liner implant includes an eversion-resistance zone adapted to reduce the likelihood of eversion of the liner in a proximal direction (i.e., toward the stomach). Without precautions, a negative pressures or reverse peristalsis within the intestine (e.g., when vomiting) will tend to push the liner back through the anchor. The eversion resistance zone can be provided by reinforcing a region of the liner, just distal to the anchor. Liners having eversion resistant features are described in U.S. patent application Ser. No. 11/147,984, filed on Jun. 8, 2005 claiming priority to Provisional Application No. 60/645,296 filed on Jan. 19, 2005 incorporated herein by reference in their entireties.

The liner 210 can include one or more restrictive elements 215a, 215b (generally 215) positioned therein to partially block the intestinal lumen thereby impeding the flow of chyme and subsequently delaying emptying of the stomach. The restrictive elements 215 can include diaphragms that provide a partial blockage within the liner. For example, the diaphragm can be formed from an impermeable membrane defining an aperture or orifice that is smaller than the diameter of the liner 210. The diaphragms can have different orientations and configurations adapted to produce a desirable resistance to the flow of chyme within the liner 210.

The anchored liner 210 provides a framework for positioning and securing the diaphragms 215. As illustrated, a first diaphragm 215a is attached to the liner at a first distance $L_1$ measured distally from the proximal end of the liner. A second diaphragm 215b can optionally be attached to the liner 210 at a second distance $L_2$ measured distally from the first diaphragm 215a. The distal end of the liner 210 can terminate at the location of the last diaphragm 215 or optionally may extend further as illustrated.

Exemplary diaphragms 215 are described below and can be attached to the liner using any suitable method of attachment. For example, the diaphragms 215 can be attached using chemical fastening means, such as adhesives or thermal bonding. Alternatively or in addition, the diaphragms 215 can be attached using mechanical fastening means, such as sutures, staples, and clips.

The diaphragm 215 can take on any conceivable shape. Exemplary diaphragms are shown in FIGS. 4A through 4D. A diaphragm 300 defining a single aperture or orifice 305 is shown in FIG. 4A. The orifice 305 is defined within a diaphragm providing a closed surface 300. The orifice 305 provides a reduced-diameter stricture.

An alternative embodiment is a partial-block diaphragm 310 is shown in FIG. 4B. The partial-block diaphragm 310 is shaped and positioned to block a portion of the intestinal lumen. As shown, the partial-block diaphragm 310 can include a planar surface bounded between a chord 312 and the perimeter of the adjacent liner 314. Selection of the chord controls the surface area of the bounded diaphragm 310 and subsequently controls the percent blockage provided. For example, selection of a chord 312 corresponding to a diameter of the circular arc will result in a 50% blockage. More generally, the shape of the partial-block diaphragm 310 can take on other forms and need not be limited to the exemplary shape described herein.

In another embodiment shown in FIG. 4C, the diaphragm 320 includes more than one smaller orifices 325. The number and size of the orifices 325 can be used to control the percent blockage of the lumen resulting in resistance to the flow of chyme. Additionally, the diameter of the orifices 325 themselves can be used to provide further resistance by limiting the size of solids allowed to pass. For example, multiple circular orifices 325 can be distributed in a regular or irregular pattern across the surface of the diaphragm 320.

In some embodiments, the diameter of the diaphragm is about 25 mm, corresponding to the internal diameter of the liner 210, with each orifice 325 having a respective smaller diameter (e.g., about 3 millimeters or less). Alternatively or in addition, the size of the aperture can be increased by removing one or more portions of the diaphragm between groups of orifices 325. Such alterations can be accomplished prior to implantation of the device, or in situ using an endoscope. The material can be removed or the aperture otherwise enlarged by selectively cutting the material between different apertures. In some embodiments, perforations 326 are provided between different orifices 325 and along the diaphragm itself to facilitate alterations.

In yet other embodiments, the diaphragm 330 includes a screen or sieve as illustrated in FIG. 4D. A screen or sieve 335 can be coupled to a frame 330 to facilitation attachment to the diaphragm 330 to the liner 210

Figure 5:
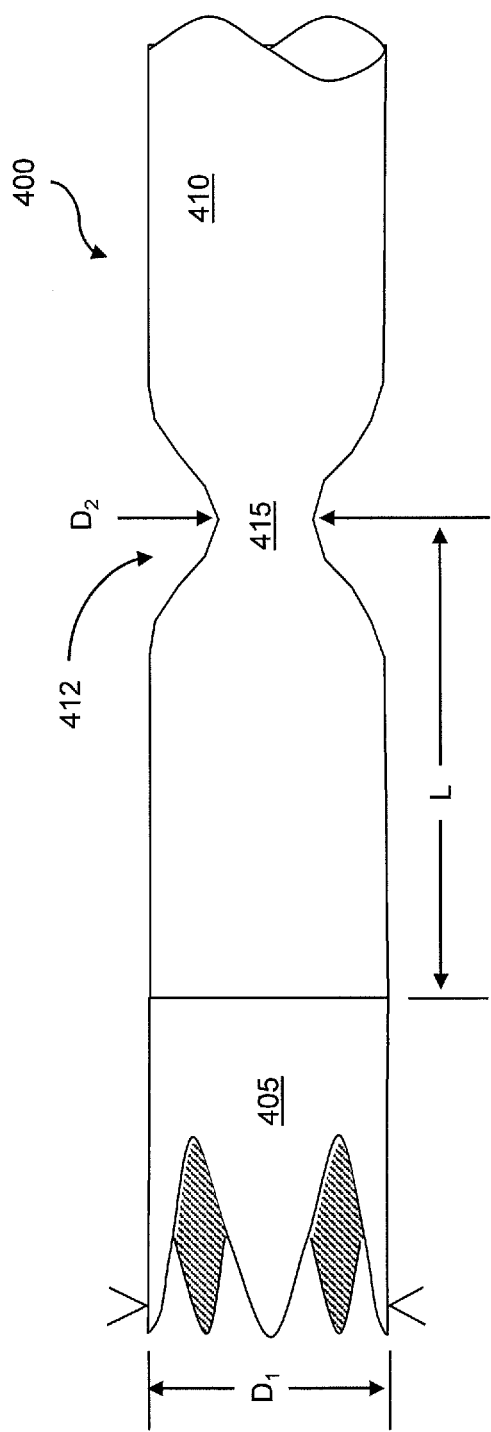
FIG. 5 is a schematic diagram illustrating an embodiment of the invention including a liner having a narrowed region.

Alternatively or in addition, an artificial stricture can be created within the liner itself. An exemplary liner-based stricture device 400 is shown in FIG. 5. The device 400 includes an elongated liner 410 having an internal diameter and defining a reduced diameter over at least a portion of the liner length. In some embodiments, the device 400 includes an anchor 405 coupled to the proximal end of the elongated liner 410 to retain the device within the gastrointestinal tract when implanted therein as described above. The liner 410 contains an axial region 412 having a reduced diameter to provide a permanent restrictor 415. For instance, the liner 410 could be reduced in diameter forming the hourglass configuration shown. Thus, the elongated liner's diameter measured along its axis transitions from a first diameter $D_1$ (e.g., 25 millimeters), at a proximal end and for a predetermined length L along the liner, to a lesser diameter $D_2$ (e.g., about 3 to 10 millimeters). The reduced diameter persists at least briefly, and then may or may not transition back again to a larger diameter (e.g., back to $D_1$).

In some embodiments the lesser diameter (e.g., $D_2$) persists for only a short distance resulting in the hourglass configuration; whereas, in other embodiments the reduced diameter may extend for a predetermined length along the axis. The resulting reduced diameter provides a permanent stricture, or narrowed orifice, tending to slow gastric emptying by reducing the rate at which chyme flows through the orifice and consequently through any portion of the intestine proximal to the orifice.

In another embodiment, not shown, substantially the entire length of the liner can be sized having a diameter smaller than would otherwise be provided by the intestine alone. For example, a liner defining a central lumen with a diameter less than 25 millimeters (e.g., between about 5 and 20 millimeters) would also impede the flow of chyme by increasing its flow resistance.

Figure 6:
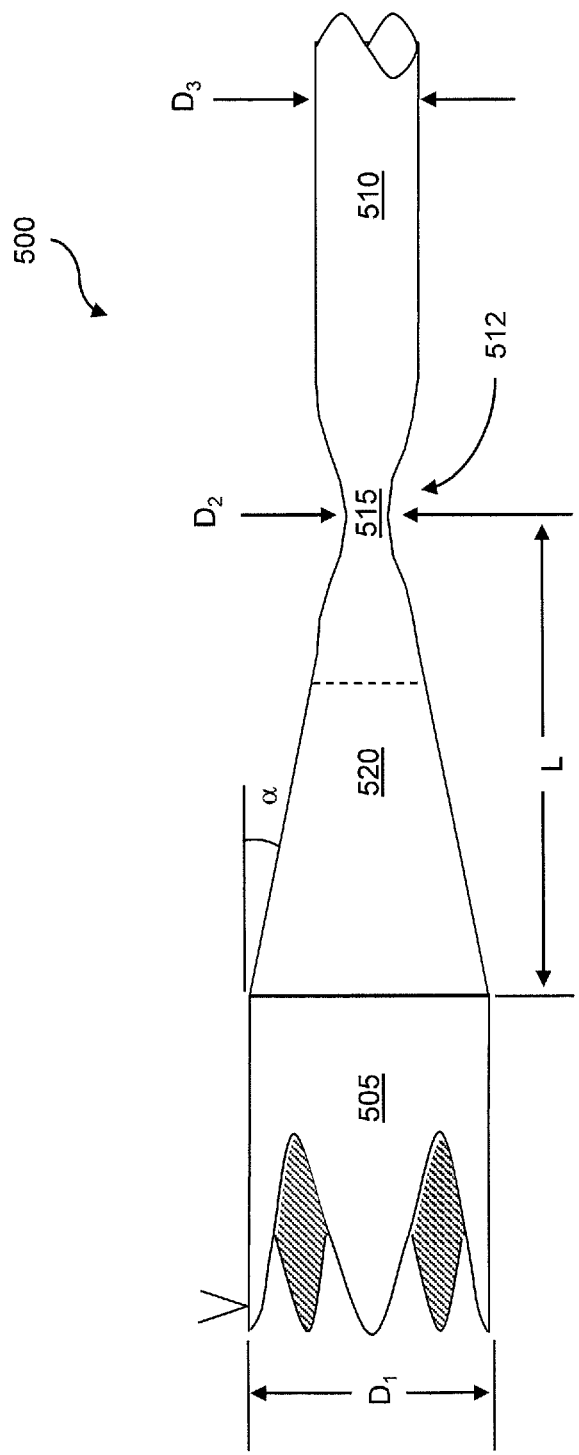
FIG. 6 is a schematic diagram illustrating an alternative embodiment of the invention including a tapered segment and a narrowed region.

In an alternative embodiment shown in FIG. 6, an implantable device 500 includes a restrictor formed by a liner 510 coupled at its proximal end to an anchor 505 adapted to anchor the liner with the gastrointestinal tract. In particular, the device 500 includes an aperture 515 having a reduced diameter $D_2$, similar to that describe above in relation to FIG. 5. Additionally, however, the device 500 includes a tapered liner segment 520 between the anchor and the aperture 515. The tapered segment 520 transitions a first diameter $D_1$ to a lesser diameter by "necking down" a proximal portion of the device. The tapered segment 520 can be accomplished in a reinforced region of the liner just distal to the anchor 505 (e.g., the eversion-resistant feature). Such a restrictor provides a permanent orifice, of a diameter less than the natural lumen, thereby slowing gastric emptying. It is believed that the tapered region 520 will reduce the loss of water from the chyme suspension that might otherwise occur in a more abrupt transition.

Alternatively or in addition, the length of the liner can slow gastric emptying. Some test observations indicate that animals having longer liner implants (e.g., 4 ft, or about 1.2 meters) appear to eat less, or at least less quickly, than do animals with similar, but shorter liners (e.g., 2 ft, or about 0.6 meters). At least one reason that the length of the liner matters is that the longer the liner, the slower the propagation of chyme through it. An animal may have a greater sense of fullness as the chyme winds through the intestines more slowly. Also, the intestines may need to work harder to pass the chyme. Thus, the liner length can affect energy expenditure directly.

Abrupt restrictions, such as those provided by the hourglass taper (FIG. 5) and the diaphragm (FIGS. 3 and 4) are focal restrictions in that they transition from a larger diameter to a smaller diameter over a relatively short distance. One disadvantage of such focal restrictions is that they may lead to an abrupt and unwanted separation of water from the chyme suspension at the orifice, making the chyme thicker and more difficult to pass. One means of avoiding this unwanted removal of water is to provide a liner that is tapered gradually over its length.

Figure 7:
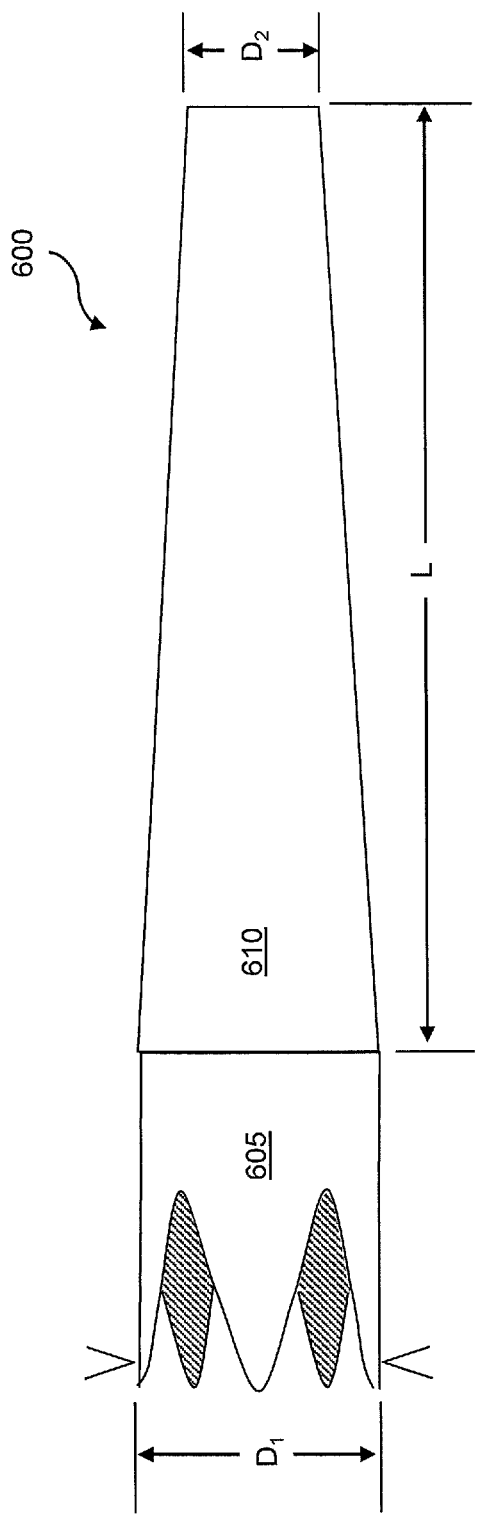
FIG. 7 is a schematic diagram illustrating an embodiment of the invention including a tapered liner.

As shown in FIG. 7, an implantable device 600 includes a liner 610 coupled at its proximal end to an anchor 605, which is adapted to anchor the device 600 within the gastrointestinal tract. The liner provides a first diameter $D_1$ at its proximal end closer to the stomach and a second diameter $D_2$ that is less than the first diameter at its distal end, further from the stomach. Thus, the diameter of the liner varies or tapers between the first and second diameters along a length L. The particular profile of the taper is selectable and can be chosen, for example, at the time the liner is formed. Thus, the diameter of the liner can change along its length in a linear fashion, as shown. Alternatively or in addition, the diameter can change along the length of the liner according to one or more other mathematical functions including polynomial, exponential, and/or logarithmic functions. Preferably, the chyme would remain well hydrated through the liner until the distal end where a larger restriction would lie.

Figure 8A:
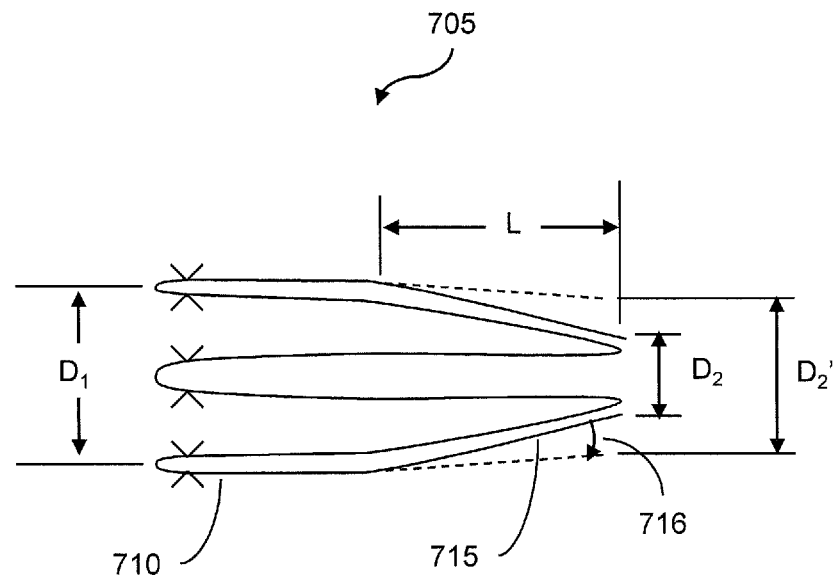
FIG. 8A is a schematic diagram illustrating an embodiment of a tapered anchor.

Illustrated in FIG. 8A is a schematic diagram of an embodiment of the invention including a tapered anchor 705. The anchor 705 can be formed providing a proximal opening 710 having a first diameter $D_1$ and a distal opening 715 having a second diameter $D_2$ that is less than the first. The anchor 705 can be formed from rigid or semi-rigid material. For example, the anchor can be formed from an alloy, such as stainless steel or Nitinol. In some embodiments, at least the distal region of the anchor is resilient, temporarily expanding to pass material sized larger than the second diameter therethrough, then returning to its reduced diameter. For example, the distal opening 715 can flex outward, temporarily opening to a larger diameter $D_2'$ when subjected to an expanding force 716 due to elevated internal pressure above about 75 in $H_2O$. This would permit the anchor to open if it became obstructed with a large food particle and relieve the obstruction as the stomach forces chyme through at elevated pressure. Tapered anchors 705 can be combined with any of the other features described herein including a liner and one or more diaphragms. When combined with a liner, sufficient excess liner material is provided to allow expansion of the anchor's distal end.

Figure 8B:
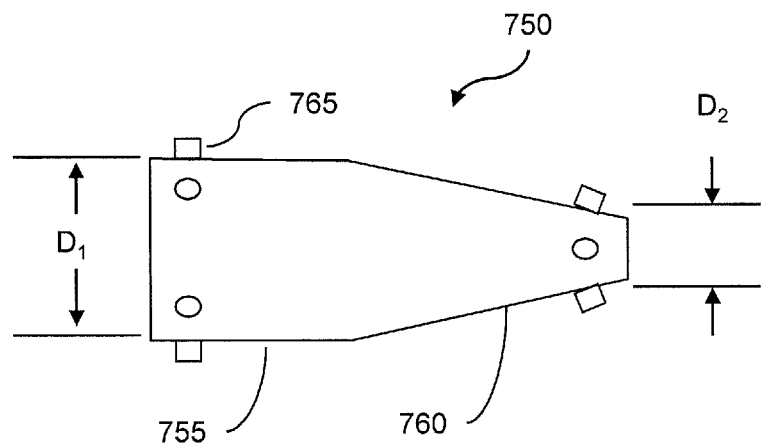
FIG. 8B is a schematic diagram illustrating an exemplary mandrel used to form the tapered anchor of FIG. 8A.

Wire anchors, such as the wave-type anchors described above can be formed by forming a wire about a mandrel. An exemplary mandrel 750 that can be used to form a tapered anchor is shown in FIG. 8B. The mandrel 750 is shaped according to a desired taper profile having a first diameter $D_1$ at its proximal end 755 and a tapered region leading to a reduced diameter $D_2$ at its distal end 760. The mandrel 750 may contain other features to facilitate forming the anchor thereon. For example, the mandrel 750 shown provides a number of posts 765 about which a wire is bent to form a tapered anchor.

In some embodiments, the artificial stricture provides an adjustable orifice. For example, the adjustable orifice can be provided within a gastrointestinal liner. Thus, the diameter of the orifice can be adjusted to selectably increase and/or decrease its diameter. Varying the diameter of the orifice similarly affects the resistance offered by the device to the flow of chyme therethrough and can be advantageous for tailoring performance of the device during a particular course of treatment. For example, if a patient outfitted with an adjustable device is not losing weight sufficiently, the diameter of the orifice can be altered to vary the performance (i.e., the orifice can be narrowed to provide more restriction, ideally leading to greater weight loss). Preferably, adjustments to the orifice can be accomplished remotely or using an endoscopic procedure and without the need for surgery. Alternatively or in addition, adjustment can be accomplished through a remote, subcutaneous route.

Figure 9A:
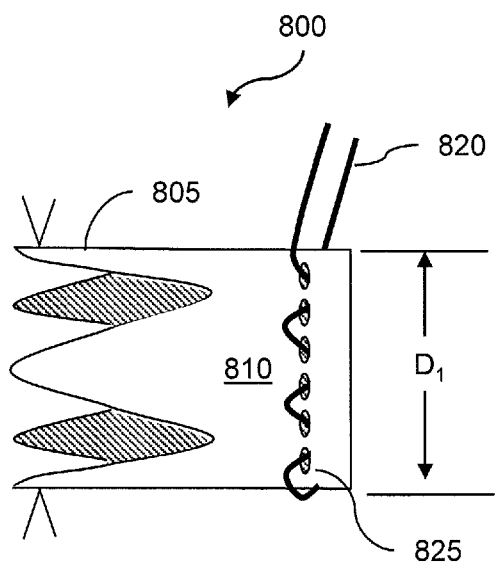
FIGS. 9A and 9C are schematic diagrams illustrating side views of an embodiment of the invention including a drawstring restrictor shown in the open and partially-closed positions, respectively.
Figure 9B:
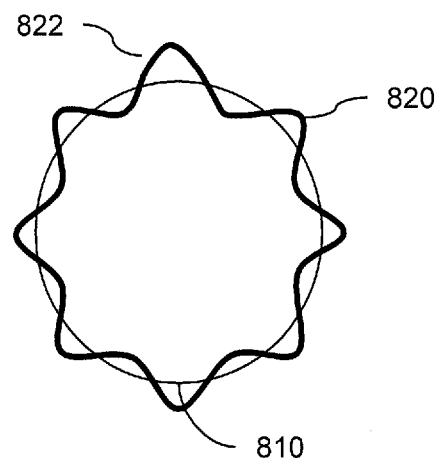
FIGS. 9B and 9D are schematic diagrams illustrating end views of the embodiment of the invention shown in FIGS. 9A and 9C, respectively in the open and partially-closed positions.
Figure 9C:
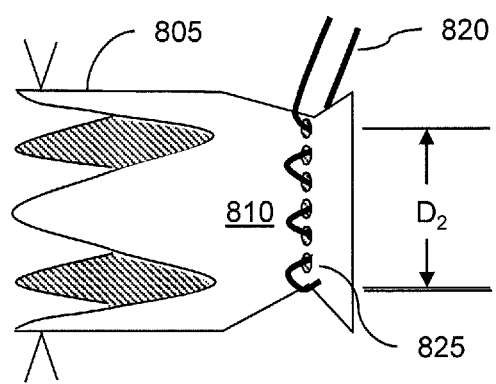

An exemplary embodiment of an artificial stricture having an adjustable orifice is illustrated in FIGS. 9A through 9D. An intestinal implant 800 includes an anchor 805 coupled to a length of liner 810. At least a portion of the liner is altered to form an adjustable orifice or restriction. As shown, the liner 810 can be altered using a drawstring 820. For example, the implant 800 includes a collapsible lumen and a drawstring. The collapsible lumen is operable by adjusting the drawstring 820 to selectively change the size of a constriction within the lumen. Thus, the drawstring can be used to alter the size of the orifice between an unconstrained diameter $D_1$ (FIG. 9A) and a reduced diameter $D_2$ (FIG. 9C). In some embodiments, the drawstring 820 is provided at a distal end of a relatively short gastrointestinal liner 810, as shown. Alternatively, the liner 810 may extend for a predetermined length and the drawstring 820 positioned at any preferred location along the length of the liner 810.

The drawstring 820 can be sewn into the liner 810 in a purse string fashion, as shown. That is, the drawstring can be laced through holes or eyelets 825 formed in the liner material and extending about the perimeter of the liner 810 (FIG. 9B). Alternatively or in addition, the drawstring can be inserted into a hem or a casing, provided within the liner 810 (not shown). Usually, when using a hem or a casing at least one access port will be necessary through which the drawstring can be grasped for adjustment.

Figure 9D:
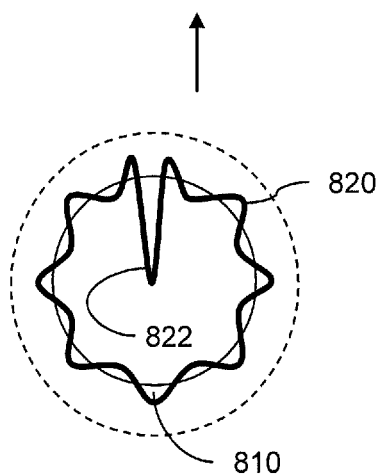

In some embodiments, the drawstring includes at least one feature adapted for grasping. For example, the drawstring can include at least one loop 822 that may extend within the interior lumen of the liner. The loop 822 can be grasped by a device and manipulated to alter the diameter of the liner. As shown in FIG. 9D, pulling the loop 822 results in a reduction of the diameter of the liner 810.

In yet other embodiments, the drawstring 820 can be used to adjust the diameter of the anchor 805 itself. For example, the drawstring 820 can be woven through the distal end portion of an anchor 805 (not shown), such that an adjustment of the drawstring 820 changes the diameter of the distal end of the anchor 805.

Once implanted, the drawstring 820 can be accessed remotely (e.g., endoscopically). An instrument, such as a hook, or pinchers can be used to grasp an exposed portion of the drawstring. Once grasped, the drawstring 820 can be adjusted to create a smaller or larger opening. For example, the drawstring 820 can be pulled away from a wall of the liner 810 (e.g., radially inward), in a proximal or distal direction along the length of the liner 810 (e.g., axially), or in a combination of both radial and axial directions.

The drawstring 820, once adjusted, can include a feature, such as a locking means, to retain the drawstring 820 in the adjusted position. It should be noted that locking the drawstring holds it in place to prohibit any further unintentional adjustment (e.g., expansion) of the orifice. Preferably, the locking means is reversible such that it can be locked, unlocked, and then locked again for re-adjustment. For example the drawstring can include a mechanical clip, or more simply a knot, suitably placed to limit further adjustment. In some embodiments a knot can be provided in the drawstring to prohibit expansion of the device beyond a maximum diameter as set by placement of the knot.

Figure 10A:
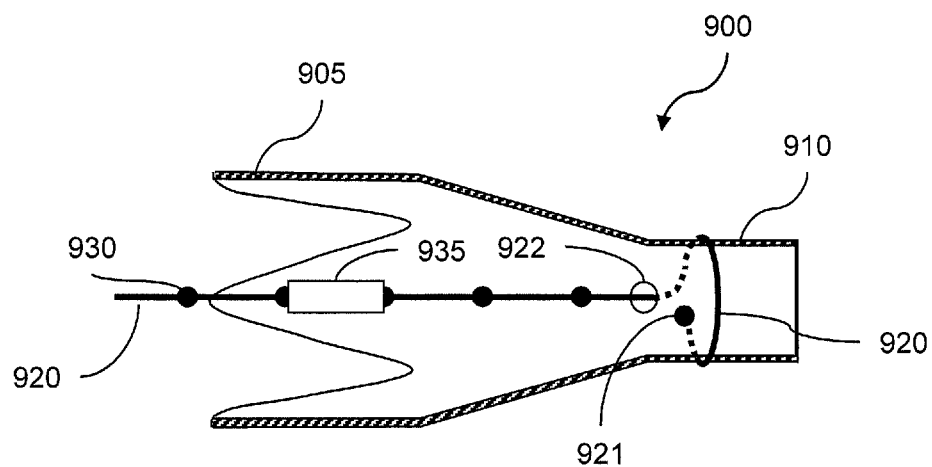
FIG. 10A is a schematic diagram illustrating a side view of an embodiment of a ball-and-cleat locking mechanism for locking the drawstring of FIGS. 9A-9D.

Shown in FIG. 10A is a cross-sectional view of an embodiment of a liner having a ball-and-cleat locking means adapted to lock a drawstring 920, once adjusted. A portion of the drawstring 920 is wrapped around a segment of the liner 910, such that the drawstring 920 can be used to narrow the interior of the liner 910. For example, one end of the drawstring 921 can be secured with respect to the liner 910. The free end of the drawstring 920 can then be wrapped about the exterior of the liner 910, forming a loop thereabout. The free end can be further threaded through an opening 922 into the interior of the liner 910. By adjusting, or pulling the free end of the drawstring 920 with respect to the secured end 921, the diameter of the loop is reduced, thereby reducing the interior diameter of the liner.

A number of balls 930, or knots, are provided along a portion of the drawstring 920 (e.g., a suture). As the drawstring 920 is adjusted, a portion of the drawstring 920 containing the ball 930 is coupled to a cleat 935 to restrict further adjustment of the drawstring. The cleat 935 can be coupled to the liner 910 or more preferably to a portion of the anchor 905.

In another embodiment (not shown), at least a proximal portion of the drawstring can be replaced by a sturdy tape with an integrated gear rack, or notched belt. A ratchet including an opening can be attached to the liner or anchor. The ratchet includes a pawl that selectively engages teeth along the belt as a free end of the belt is threaded through the ratchet. Thus, similar to a cable tie-wrap device, the drawstring can be adjusted in one direction by simply pulling the free end of the belt. Adjustment in an opposite direction is generally prohibited by the pawl.

Figure 10B:
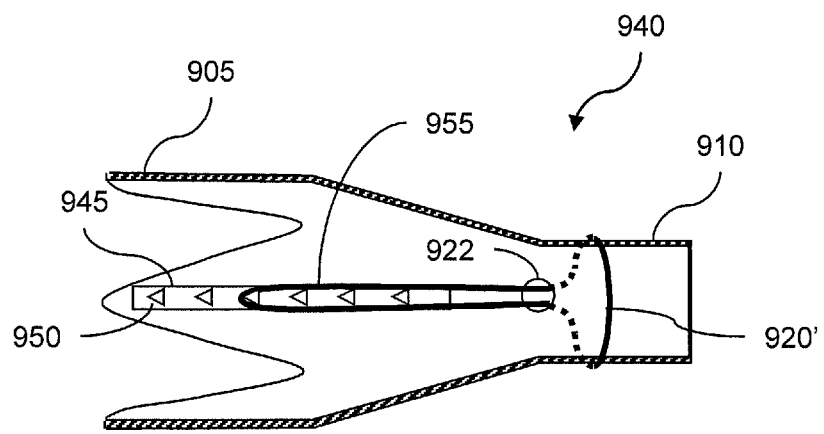
FIG. 10B is a schematic diagram illustrating a side view of an embodiment of a hook-and-eyelet locking mechanism for locking the drawstring of FIGS. 9A-9D.

FIG. 10B is a cross-sectional view of an alternative embodiment of an adjustable implant device 940 using a hook-and-eyelet locking means for locking a drawstring 920'. Thus, one or more hooks 950 are provided along a portion of the liner. A loop 955 or eyelets formed in the drawstring 920' are adapted to engage at least one of the hooks 950. A portion of the drawstring 920' is wrapped around a segment of the liner 910, such that the drawstring 920' can be adjusted to narrow the interior of the liner 910. The hooks 950 are configured to selectably engage a loop or eyelets 955 to secure the drawstring 920' once adjusted. For example, a linear array of hooks 945 can be attached to the anchor 905 and/or to the liner 910. The drawstring 920' is adjusted, as described above, and a portion of the drawstring 920' is position to engage a selected one of the array of hooks 945 corresponding to a preferred diameter of the liner 910.

Alternatively or in addition, a crimp-type locking means can be used to crimp a portion of the drawstring thereby restricting further adjustment. One embodiment of a crimp-type locking means is shown in FIG. 10C. Thus, a graspable feature 965 of a drawstring 960 is pulled through one or more crimpable elements 970. When the drawstring 960 is positioned to produce a desired aperture, at least one of the crimpable elements 970 is crimped about the drawstring 960. If further adjustment is necessary, the crimpable element 970 securing the drawstring 960 can be breached to free the drawstring 960. After further adjustment, the drawstring 960 can be secured again by crimping another one of the crimpable elements 970 to again secure the drawstring 960.

Yet another embodiment of a friction-type locking means is shown in FIG. 10D. A portion of the drawstring 960 is drawn through a resilient channel 980 that is biased in a "pinched" or closed position. Thus, referring to the cross-sectional diagram of FIG. 10E, the walls of the resilient channel 980 pinch a portion of the drawstring 960 without application of an external force, thereby maintaining the drawstring 960 in fixed position. Subsequent adjustment of the drawstring is possible by applying an external force that flexes the compliant channel (e.g., forces 981', 981" directed along the arrows of FIG. 10E) thereby counteracting its biasing force. When flexed in this manner, the resilient channel 980 conforms to an open configuration as indicated in phantom, thereby releasing its grip on the drawstring 960. Thus, the resilient channel 980 is opened (i.e., the pinch is removed), which allows the portion of the drawstring contained therein to be further adjusted. Once readjustment is completed, the external force is removed from the resilient channel 980 allowing it to revert to its biased configuration to pinch the drawstring, once again holding it fixed. In some embodiments, the resilient channel 980 includes internal features, such as teeth 985, adapted to enhance the securing force provided to the entrapped portion of the drawstring 960.

In some embodiments, as shown in FIGS. 11A and 11B, an implant 1000 includes an adjustable orifice provided by an inflatable device, such as a balloon. For example, the interior aperture 1015 of a toroidal balloon 1012 defines a central orifice having a diameter $D_2$. The adjustable orifice (e.g., balloon 1012) can be coupled to either an anchor 1005 or a liner 1010 coupled at its proximal end to the anchor 1005. As illustrated, a balloon 1012 is attached to a proximal portion of the liner 1010. In some embodiments in which the balloon 1012 is attached to the anchor 1005, without a liner 1010. The balloon 1012 can be attached to either the liner 1010 or the anchor 1005 using any suitable means of attachment including mechanical fasteners, such as sutures or clips, or chemical fasteners, such as adhesives or bonding.

To adjust the internal diameter of the toroidal balloon 1012, once implanted, an endoscope (not shown) can be inserted into the patient and directed to an area near the balloon 1012. A needle can then be passed through the endoscope to the balloon 1012. The balloon 1012 can include a septum through which the needle can access the balloon 1012. A fluid, preferably such as water, or even a gas, can be injected into or removed from the balloon 1012 selectively inflate or deflate the size of the balloon 1012, thereby adjusting the size of the orifice 1015 between different-sized apertures 1017', 1017" as shown in FIG. 11B.

In some balloon embodiments, the implant 1000 includes a small inflation/deflation tube 1025 coupled between the balloon 1012 and a remote location 1030. The tube 1025 can be used to inflate and/or deflate the balloon 1012 by allowing a fluid or gas to be transferred into or out of the balloon 1012 from the remote location 1030. In some embodiments, the small tube 1025 passes from the balloon 1012 proximally into the stomach, and through a wall of the stomach into a subcutaneous reservoir. Alternatively, the small tube 1025 passes from the balloon 1012 to an injection port 1020. Preferably, the injection port 1020 is located just below the skin 1021. Thus, a needle can be used to pierce the skin 1021 for accessing the injection port 1020. Once accessed, the needle is again used to transfer a fluid or gas between to or from the balloon 1012, thereby adjusting the size of the balloon 1012. In other embodiments, one end of the tube 1025 exits the patient. Again, fluid could be injected into or removed from the balloon through this tube 1025 to adjust the size of the opening.

In addition to simply providing a narrower channel through which chyme will flow, the liner can reduce the efficiency of natural peristalsis. Peristalsis refers to the forces exerted by the intestine to mix and pass chyme distally through the intestine. In the presence of a liner, peristaltic forces provided by the intestine must operate upon the chyme through the liner material. Preferably, the liner is adapted to channel most if not all of the chyme through its central lumen.

In some embodiments, the efficiency of peristalsis can be reduced by using a dampening liner. A dampening liner includes preferred material properties adapted to absorb and/or resist at least some of the peristaltic force provided by the intestine. Thus, liners that are thicker and/or more rigid will tend to dampen the peristaltic forces more so than thinner liners formed from the same material.

Figure 12:
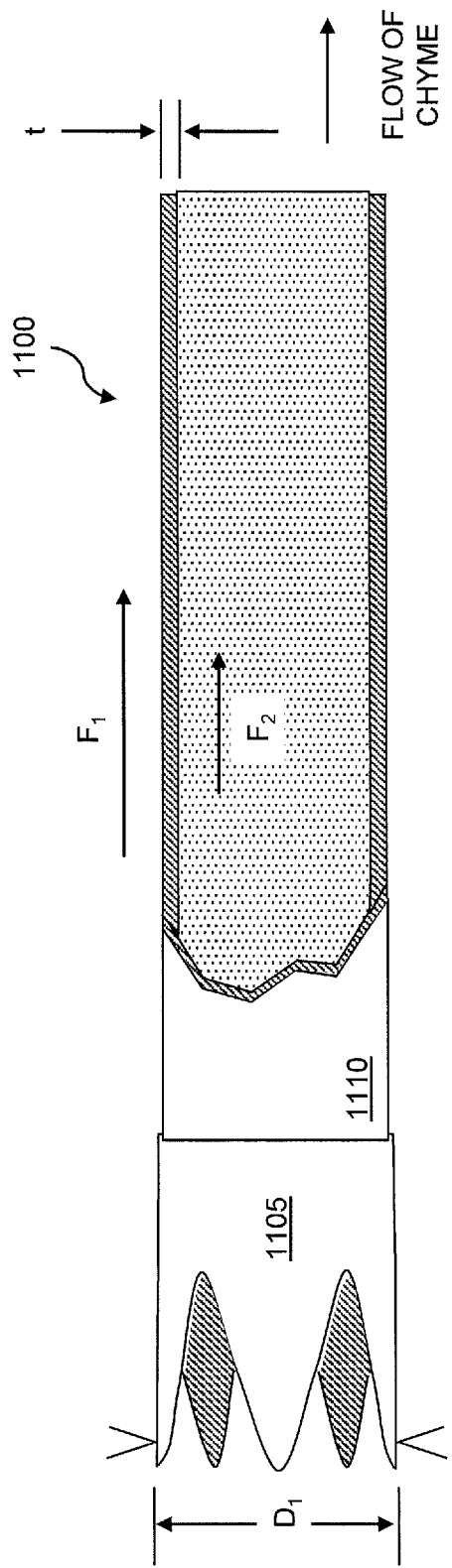
FIG. 12 is a partially-cut-away schematic diagram illustrating an embodiment of the invention providing a thick-walled liner.

Such a dampening liner can be configured for implantation within the digestive tract to reduce efficiency of peristalsis. A partially-cut-away of an embodiment of a dampening liner 1100 is shown in FIG. 12. A thick-walled liner 1110 is coupled at its proximal end to an anchor 1105 adapted for implantation within the gastrointestinal tract. The stiffer the material of the liner 1110, the less effective peristalsis will function since the forces that the intestine exerts to pass chyme $F_1$ must work through the liner material 1110. Thus the resulting forces acting upon chyme within the liner 1110 are represented by a second force $F_2$ that is less than $F_1$ due at least in part to the damping features of the liner 1110.

In some embodiments, it may be desirable to have a relatively flexible liner near the bile and pancreatic ducts so as not to block the ampulla of vater, but a stiffer material more distal, to increase resistance to flow. Thus, the properties of the liner material can be varied along the liner. For example, the same material can be provided with various thicknesses to control variations in the damping performance of the liner along its axis. Alternatively or in addition, different materials can be combined to provide the desired damping values. Configurations can include overlapping portions of the same and/or different materials and/or adjacent regions formed from different materials.

Figure 13:
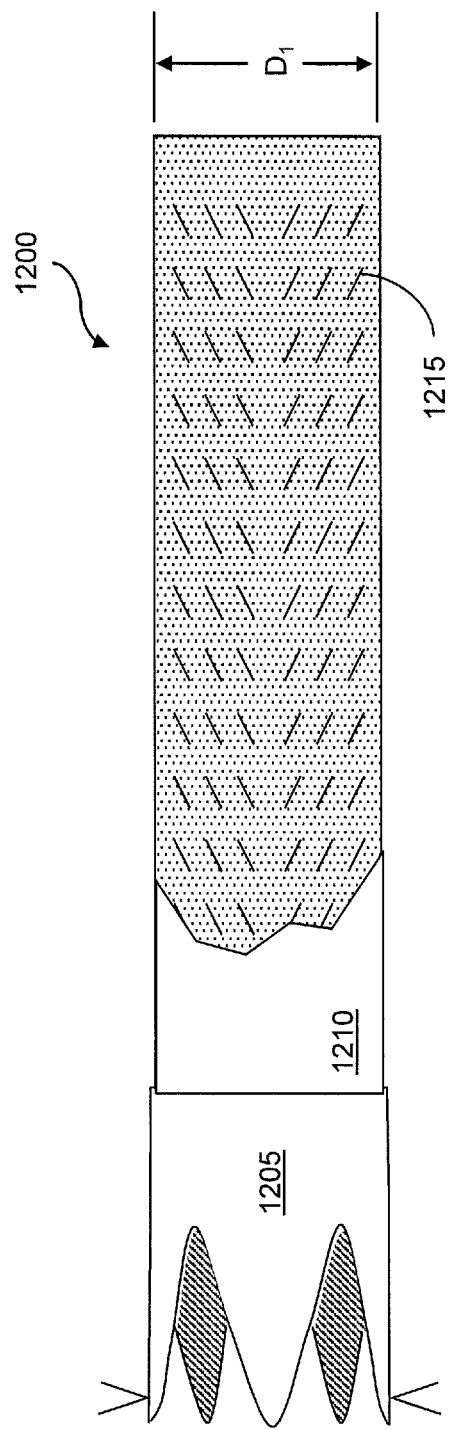
FIG. 13 is a partially-cut-away schematic diagram illustrating an embodiment of the invention providing an internal resistive surface.

Alternatively or in addition, the device can include an interior surface adapted to impede the flow of chyme. For example, as shown in the partially-cut-away schematic diagram of FIG. 13, a textured liner device 1200 includes a liner 1210 coupled at its proximal end to an anchor 1205. The interior surface of the liner 1210 wall includes surface features designed to interfere with the flow of chyme, thus acting to retard the flow against natural peristaltic forces. The surface features can include multiple artificial cilia 1215. Preferably, the artificial cilia 1215 are oriented in a proximal direction to maximize their effectiveness. The artificial cilia 1215 can be created by brushing or abrading the interior surface of the liner 1210 in a direction against the flow of chyme. This can raise a nap in the surface of the material biased to the direction of the abrasion.

Gastric emptying can also be slowed by implanting a mass having a non-negligible volume within the intestine. A blocking mass takes up room within the intestine causing a restriction of sorts within the intestine at least along the length of the mass. Consequently, progression of chyme through the intestine is slowed. The mass provides a smaller volume within the intestine within which to hold chyme as well as a smaller lumen cross-sectional area for the chyme to pass.

In an exemplary embodiment, an implantable mass 1300 shown FIG. 14A can be implanted within the duodenum to slow the progression of chyme within a portion of the intestinal lumen. In some embodiments, the mass 1300 can be implanted at least partially in other parts of the intestine that may be distal to the duodenum. The mass 1310 can include a solid material, such as a rod. The rod can be solid, braided, or have any other suitable linear construct capable of being attached to the anchoring means 1305 and extended into the intestine.

The elongated, or rod-type blocking mass 1310 is implanted axially along the duodenum, such that the available area of a cross section of the intestine is reduced by the cross-sectional area of the blocking mass, as shown in FIG. 14B. The implanted mass 1310 can also slow gastric emptying by simply occupying a portion of the available volume within the intestinal lumen. Thus, both the length and diameter of the blocking mass can be adjusted to occupy a selectable volume.

Still further, the implanted mass 1300 can reduce the efficiency of peristalsis by absorbing or blocking at least a portion of the peristaltic force applied to chyme in the vicinity of the implanted mass 1300. Thus, the density and/or compliance of the blocking mass 1300 can also be selected to suitably reduce peristaltic efficiency.

As illustrated, the blocking mass 1310 can be anchored in the intestine using a gastrointestinal anchor 1305, such as any of the anchoring devices described above. For example an anchor 1305 is attached to the proximal end of the blocking mass 1310 using any suitable attaching means. Alternatively or in addition, the blocking mass 1310 can be attached to the intestine without an attached anchor 1305. For example, the blocking mass 1310 can be attached using mechanical fasteners, such as barbs, clips, sutures, staples, etc. As suturing to an intestine can be difficult, the sutures can extend from the implant within the intestinal lumen, through the intestine wall, and to another portion of the anatomy located outside of the intestine. Preferably, the mechanical fasteners couple to muscular tissue to securely anchor the device 1300. Alternatively or in addition, the blocking mass 1310 can be attached using other attaching means, such as chemical fasteners (e.g., surgical adhesives).

Figure 15:
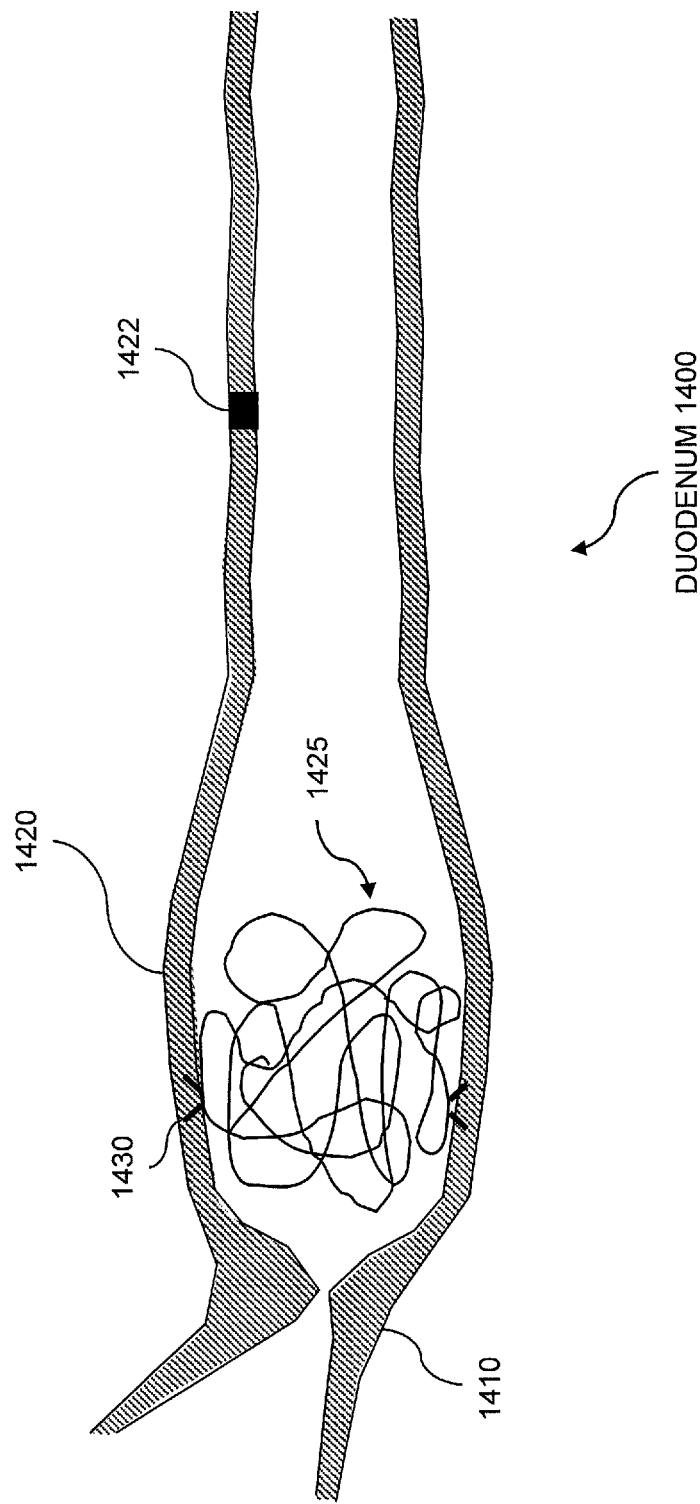
FIG. 15 is a schematic diagram illustrating a cross-sectional view of an embodiment of the invention using a filter.

In yet another embodiment, an aperture can be formed from one or more contorted elongated elements, such as bent wires. An exemplary embodiment is shown in the axial cross section of FIG. 15. One or more elongated members 1425 (i.e., wires) can be twisted in an irregular, convoluted manner to produce resistance to the passage of chyme. The resistance is due at least in part to reduced apertures or screen formed by overlapping portions of the convoluted wire 1425. In some embodiments the wire is a metal wire, such as a metal alloy. In a preferred embodiment, the wire is a Nickel-Titanium alloy referred to as a Nitinol. The wire can be anchored within the intestine using any suitable anchoring means 1430, such as mechanical fasteners, barbs, sutures, etc. In some embodiments, the implanted wire provides sufficient force for an interference fit keeping it in place. Anchoring can be enhanced with any of the above anchoring means by locating the anchor 1420 in a proximal portion of the duodenum 1400, just distal to the pyloric sphincter 1420 and proximal to the ampulla of vater 1422, referred to as the duodenal bulb 1420.

Figure 16A:
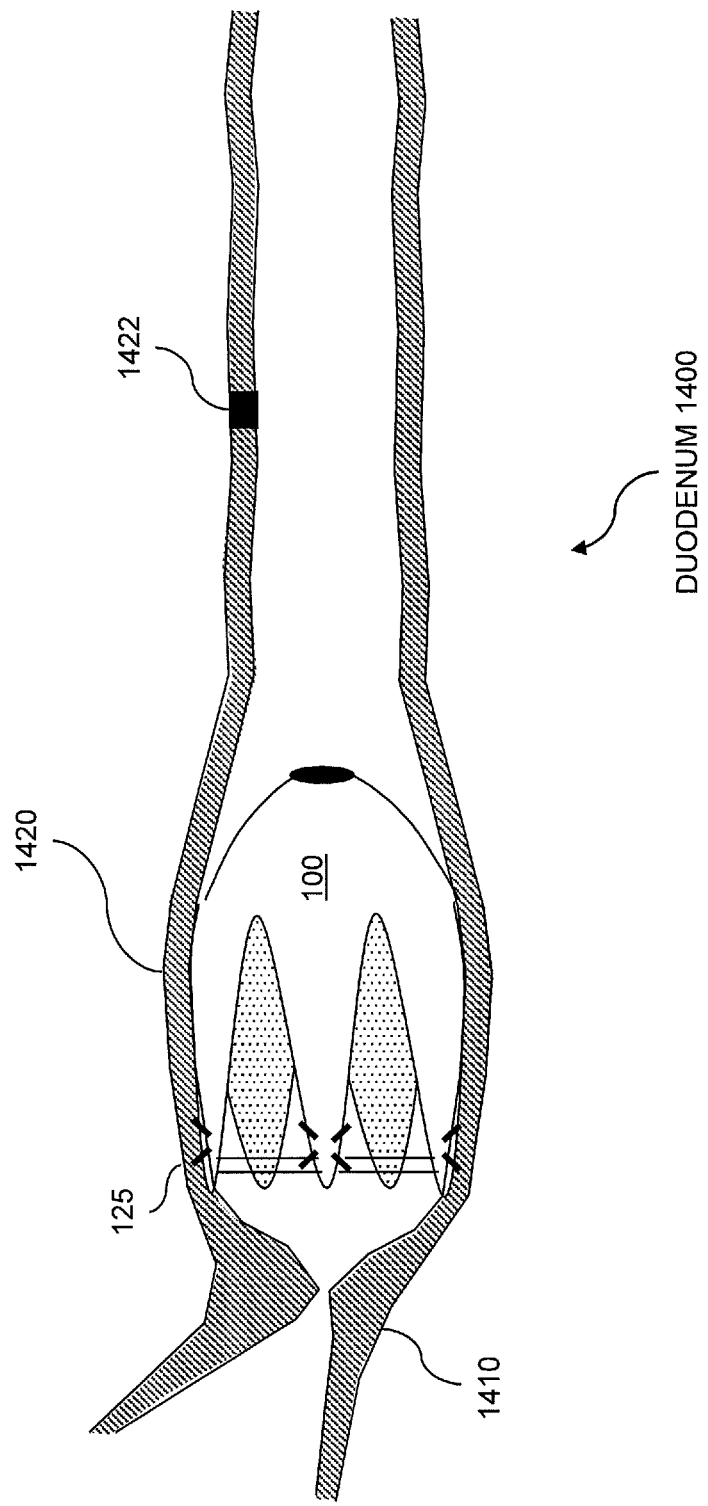
FIG. 16A is a schematic diagram illustrating the artificial structure of FIG. 1A implanted within the proximal duodenum.

A cross section of a proximal duodenum 1400 is illustrated in FIG. 16A including an artificial stricture 100 (FIG. 1A) implanted therein. The stricture is positioned distal to the pylorus 1410 and proximal to the ampulla of vater 1422, in the duodenal bulb 1420. The stricture 100 includes barbs 125 that are sized to engage muscular tissue of the intestine. The radial expansive force of the anchor maintains the proximal end of the stricture 100 sealably engaged with the interior walls of the duodenal bulb 1420. The radial force is also sufficient to keep the barbs 125 firmly implanted within the surrounding tissue. Chyme emptying into the duodenum 1400 through the pylorus 1420 encounters the artificial stricture 100. The reduced aperture of the stricture decreases the rate at which chyme passes into the distal duodenum 1400. As chyme continues to empty from the stomach, the chyme builds up along a proximal side of the stricture 100. Thus, the stomach empties at a slower rate than would otherwise occur without the stricture due to its reduced aperture of the stricture 100. Exemplary fluid flow rates can be 2 cm/sec through a 25 mm diameter opening.

The stricture material 100 may be constructed of a compliant or non-compliant polymer. If non-compliant, such as 0.0005" thick ePTFE and FEP, then the hole size remains fixed and also can be dilated with a balloon as it will plastically deform. If compliant, such as with 0.015" thick, 40-60 A durometer silicone, the hole may enlarge in response to elevated pressures that result when the hole gets obstructed by large food particles.

Another means to provide a self-clearing restriction is if a compliant band is placed around the liner or outlet. One such concept would be made if the drawstring 820 of FIG. 9C were replaced with a loop about 3 mm in diameter formed using a thin elastomeric band. If the orifice becomes obstructed, stomach pressure would rise and the elastomeric band may increase in diameter and relieve the obstruction.

Figure 16B:
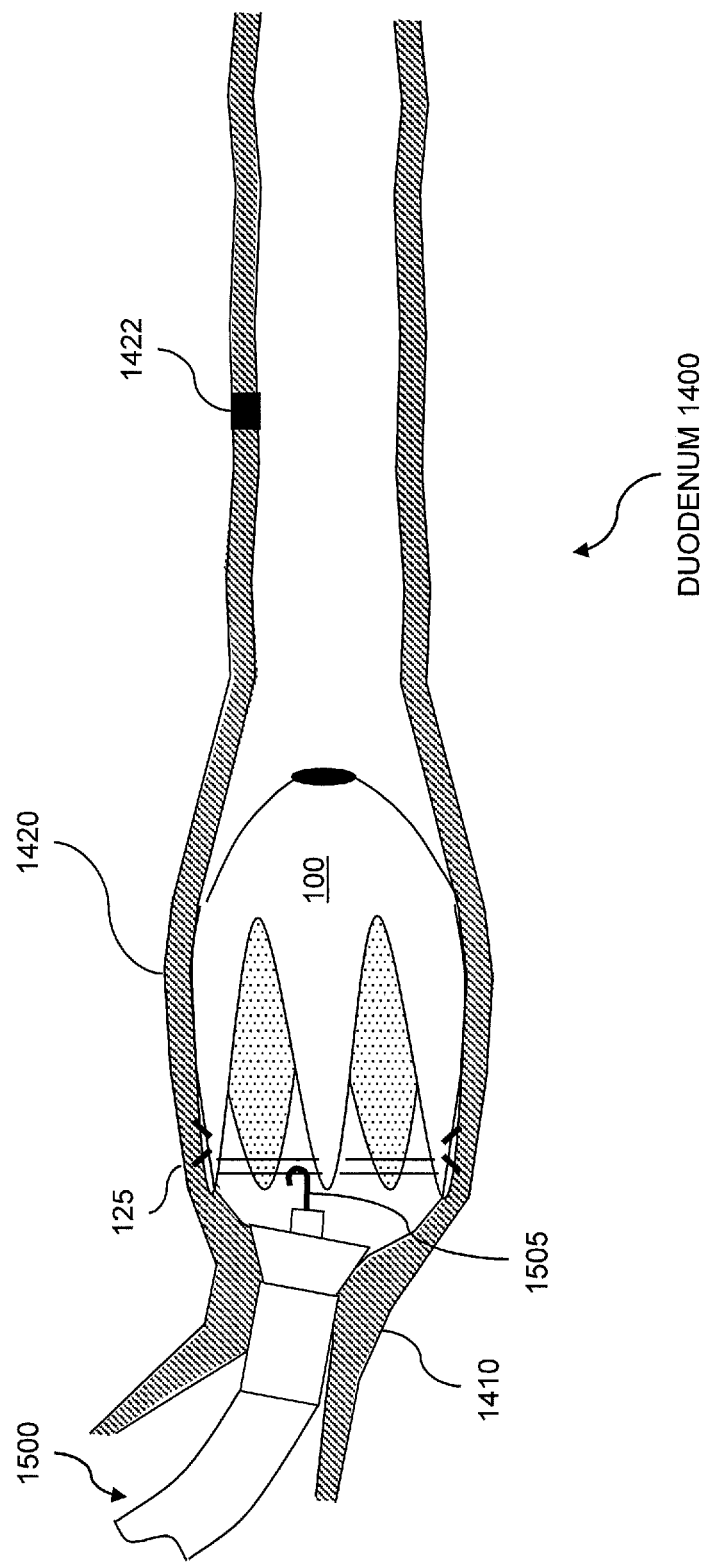
FIG. 16B is a schematic diagram illustrating a repositioning device engaging the artificial stricture of FIG. 1A.

As described above, the artificial stricture 100 can include a drawstring 125 to assist in the repositioning or removal of the device 100. As shown in FIG. 16B, a repositioning device 1500 having a grasping element 1505 can be inserted into the body to grasp a portion of the device 100. For example, the repositioning device 1500 can be inserted endoscopically through the stomach and at least partially through the pylorus 1420 to a region near the proximal end of the implanted device 100. The grasping element 1505 can then be manipulated to engage the drawstring 125 of the device 100 for repositioning or removal.

While this invention has been particularly shown and described with references to preferred embodiments thereof, it will be understood by those skilled in the art that various changes in form and details may be made therein without departing from the scope of the invention encompassed by the appended claims. It should also be appreciated that the various features of the embodiments that have been described may be combined in various ways to produce numerous additional embodiments. Moreover, while various materials, dimensions, shapes, implantation locations, types of anchors, etc. have been described for use with the disclosed embodiments, others besides those disclosed may be utilized without extending the scope of the invention, including implantation locations in or above the pylorus.

What is claimed is:

1. A gastrointestinal implant comprising:
   an anchor configured for implantation within a gastrointestinal tract of an animal at a position distal to the animal's pylorus;
   a collapsible, elongated liner coupled to the anchor, the liner formed from a substantially non-permeable material, the anchor and liner defining a lumen through which chyme passes, the liner being thin and unsupported beyond the anchor and tending to collapse upon itself when empty; and
   an orifice in communication with the anchor, the orifice retained at between 3 mm and 5 mm in diameter, the orifice being a hole in a membrane positioned within and across the lumen, the anchor removably securing the liner and membrane in position and the membrane retarding the outflow of chyme from the stomach.

2. The gastrointestinal implant of claim 1, wherein the orifice is adjustable to selectively vary resistance provided to the outflow of chyme from the stomach.

3. The gastrointestinal implant of claim 1, wherein the liner has a non-uniform diameter along its axis.

4. The gastrointestinal implant of claim 3, wherein the liner includes an axial length having a reduced diameter that is bounded on either end by an adjacent portion of liner having a greater diameter.

5. The gastrointestinal implant of claim 1, wherein the liner material reduces effectiveness of peristaltic forces.

6. The gastrointestinal implant of claim 1, wherein the anchor comprises a radial spring adapted to sealably engage tissue of the gastrointestinal tract.

7. The gastrointestinal implant of claim 1, wherein the anchor comprises at least one barb adapted for insertion into muscular tissue of the gastrointestinal tract.

8. The implant of claim 1, wherein the membrane is elastomeric.

9. The implant of claim 1, wherein the membrane comprises plastically deformable material.

10. The implant of claim 1, wherein the anchor is self-expanding and has a relaxed diameter of at least 40 mm.

11. The implant of claim 1, wherein the anchor is self-expanding and has a relaxed diameter of at least 45 mm.

12. The implant of claim 11, wherein the anchor is a wave anchor.

13. The gastrointestinal implant of claim 1, comprising plural holes in the membrane.

14. A gastrointestinal implant comprising:
   an anchor configured for implantation within a gastrointestinal tract of an animal at a position distal to the animal's pylorus;
   a collapsible, elongated liner coupled to the anchor, the liner formed from a substantially non-permeable material, the anchor and liner defining a lumen through which chyme passes, the liner being thin and unsupported beyond the anchor and tending to collapse upon itself when empty; and
   an orifice in communication with the anchor, the orifice retained at less than 10 millimeters in diameter, the orifice being a hole in a membrane positioned within and across the lumen, the anchor removably securing the liner and membrane in position and the membrane retarding the outflow of chyme from the stomach, the membrane being elastomeric and the orifice being able to temporarily expand under pressure from the chyme.

15. The implant of claim 14, wherein the orifice is between 3 mm and 5 mm in diameter.

16. The implant of claim 14, wherein the anchor is self-expanding and has a relaxed diameter of at least 40 mm.

17. The implant of claim 14, wherein the anchor is self-expanding and has a relaxed diameter of at least 45 mm.

18. The implant of claim 17, wherein the anchor is a wave anchor.

19. The gastrointestinal implant of claim 14, comprising plural holes in the membrane.

20. The gastrointestinal implant of claim 14, wherein the liner has a non-uniform diameter along its axis.

21. The gastrointestinal implant of claim 20, wherein the liner includes an axial length having a reduced diameter that is bounded on either end by an adjacent portion of liner having a greater diameter.

22. The gastrointestinal implant of claim 14, wherein the anchor comprises a radial spring adapted to sealably engage tissue of the gastrointestinal tract.

23. The gastrointestinal implant of claim 14, wherein the anchor comprises at least one barb adapted for insertion into muscular tissue of the gastrointestinal tract.

24. A gastrointestinal implant comprising:
   an anchor configured for implantation within a gastrointestinal tract of an animal at a position at or distal to the animal's pylorus;
   a collapsible, elongated liner coupled to and removably secured by the anchor, the liner formed a substantially non-permeable material, the anchor and liner defining a lumen through which chyme passes, the liner being thin and unsupported beyond the anchor and tending to collapse upon itself when empty; and
   a diaphragm having plural orifices and being positioned within and across the lumen to provide partial blockage.

25. The gastrointestinal implant of claim 24, wherein the diaphragm is formed from a membrane and the plural orifices comprise plural orifices in the membrane.

26. The gastrointestinal implant of claim 24, wherein each of the plural orifices is less than 10 mm in diameter.

27. The gastrointestinal implant of claim 24, wherein each of the plural orifices is 5 mm in diameter or less.

28. The gastrointestinal implant of claim 24, wherein each of the plural orifices is 3 mm in diameter or less.

29. The gastrointestinal implant of claim 24, wherein the diaphragm includes a screen and the plural orifices comprise plural orifices in the screen.

30. The gastrointestinal implant of claim 24, wherein the plural orifices comprise plastically deformable material.

31. The gastrointestinal implant of claim 24, wherein the liner includes an axial length having a reduced diameter that is bounded on either end by an adjacent portion of liner having a greater diameter.

32. The gastrointestinal implant of claim 24, wherein the anchor comprises a radial spring adapted to sealably engage tissue of the gastrointestinal tract.

33. The gastrointestinal implant of claim 24, wherein the anchor comprises at least one barb adapted for insertion into muscular tissue of the gastrointestinal tract.

34. The gastrointestinal implant of claim 24, wherein the anchor is self-expanding and has a relaxed diameter of at least 40 mm.

35. The gastrointestinal implant of claim 34, wherein the anchor comprises a wave anchor.

\* \* \* \* \*